(12) United States Patent
Adelson et al.

(10) Patent No.: US 8,932,832 B2
(45) Date of Patent: Jan. 13, 2015

(54) METHODS AND COMPOSITIONS RELATED THERETO FOR DETECTING AND IDENTIFYING DISTINCT SPECIES OF NUCLEIC ACIDS FROM CAUSATIVE AGENTS

(75) Inventors: Martin E. Adelson, East Windsor, NJ (US); Melanie Feola, Cherry Hill, NJ (US); Jason Trama, Burlington, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 13/199,380

(22) Filed: Aug. 26, 2011

(65) Prior Publication Data
US 2012/0064509 A1 Mar. 15, 2012

Related U.S. Application Data

(63) Continuation of application No. 11/246,976, filed on Oct. 7, 2005, now Pat. No. 8,030,032.

(60) Provisional application No. 60/616,723, filed on Oct. 7, 2004.

(51) Int. Cl.
*C07H 21/04* (2006.01)
*C12Q 1/70* (2006.01)

(52) U.S. Cl.
CPC .................................... *C12Q 1/705* (2013.01)
USPC ...................... 435/91.2; 536/24.32; 536/24.33

(58) Field of Classification Search
CPC .............................. C12Q 1/705; C12Q 1/6806
USPC ................................... 435/91.2, 24.32, 24.33
See application file for complete search history.

(56) References Cited

U.S. PATENT DOCUMENTS 5,648,079 A * 7/1997 Burke et al. ............... 424/186.1

OTHER PUBLICATIONS

Schalasta et al., Infection, vol. 28, pp. 85-91, 2000.*
Lowe et al., Nucleic acids Research, vol. 18, pp. 1757-1761, 1990.*

\* cited by examiner

*Primary Examiner* — Cynthia B Wilder
(74) *Attorney, Agent, or Firm* — Siu K. Lo

(57) ABSTRACT

Methods are described herein for detecting and identifying distinct species of nucleic acids, in a single container, for example, from a certain genus of infectious agents or otherwise causative agents comprising, for example, providing a forward PCR primer common to a homologous gene region between the distinct species, and providing a reverse PCR primer common to a homologous gene region between the distinct species, to thereby define a PCR target region amongst the species, and providing a first oligonucleotide probe specific to a nucleic acid sequence within the target region that is characteristic of a first species, providing a second oligonucleotide probe specific to a nucleic acid sequence within the target region that is characteristic of a second species, wherein the first and second oligonucleotide probes are each detectably labeled with distinctly different detectable labels, conducting a PCR reaction in the container by means of the primers to amplify the target region amongst the species, and detecting the distinct labels, thereby identifying distinct species of nucleic acids corresponding to distinct species of infectious agents. Methods are preferred, for example, wherein the infectious agent is a member of the Herpesviridae family.

2 Claims, 4 Drawing Sheets

FIG.1

```
ATCACAGGTCGTCCTCGTCGGCGTCACCGTCTTTGTTGGGAACTTGGGTGTAGTTGGTGTTGCGGCGCTTGCGCA
TGACCATGTCGGTGACCTTGGCGCTGAGCAGCGCGCTCGTGCCCTTCTTCTTGGCCTTGTGTTCCGTGCGCTCCA
TGGCAGACACCAGGGCCATGTACCGTATCATCTCCCGGGCCTCGGCTAGCTTGGCCTCGTCAAAGTCGCCGCCCT
CCTCGCCCTCCCCGGACGCGTCCGGGTTGGTGGGGTTCTTGAGCTCCTTGGTGGTTAGCGGGTACAGGGCCTTCA
TGGGGTTGCTCTGCAGCCGCATGACGTAGCGAAAGGCGAAGAAGGCCGCCGCCAGGCCGGCCAGGACCAACAGAC
CCACGGCCAGCGCCCCAAAGGGGTTGGACATGAAGGAGGACACGCCCGACACGGCCGATACCACGCCGCCCACGA
TGCCCATCACCACCTTGCCGACCGCGCGCCCCAGGTCGCCCATCCCCTCGAAGAACGCGCCCAGGCCCGCAAACA
TGGCGGCGTTGGCGTCGGCGTGGATGACCGTGTCGATGTCGGCGAAGCGCAGGTCGTGCAGCTGGTTGCGGCGCT
GGACCTCCGTGTAGTCCAGCAGGCCGCTGTCCTTGATCTCGTGGCGGGTGTACACCTCCAGGGGACAAACTCGT
GATCCTCCAGCATGGTGATGTTGAGGTCGATGAAGGTGCTGACGGTGGTGATGTCGGCGCGGCTCAGCTGGTGGG
AGTACGCGTACTCCTCGAAGTACACGTAGCCCCCACCGAAGGTGAAGTAGCGCCGGTGTCCCACGGTGCACGGCT
CGATCGCATCGCGCGTCAGCCGCAGCTCGTTGTTCTCCCCAGCTGCCCCTCGACCAACGGGCCCTGGTCTTCGT
ACCGAAAGCTGACCAGGGGCGGCTGTAGCAGGCCCCGGGCCGCGAGCTGATGCGCATCGAGTTTTGGACGATCA
CGTTGTCCGCGGCGACCGGCACGCACGTGGAGACGGCCATCACGTCGCCGAGCATCCGCGCGCTCACCCGCCGGC
CCACGGTGGCCGAGGCGATGGCGTTGGGGTTCAGCTTGCGGGCCTCGTTCCACAGGGTCAGCTCGTGATTCTGCA
GCTCGCACCACGCGATGGCAACGCGGCCCAACATATCGTTGACATGGCGCTGTATGTGGTTGTACGTAAACTGCA
GCCTGGCGAACTCGATGGAGGAGGTGGTCTTGATGCGCTCCACGGACGCGTTGGCGCTGGCCCCGGGCGGCGGGG
GCGTGGGGTTTGGGGGCTTGCGGCTCTGCTCGCGGAGGTGTTCCCGCACGTACAGCTCCGCGAGCGTGTTGCTGA
GAAGGGGCTGGTACGCGATCAGAAAGCCCCCATTGGCCAGGTAGTACTGCGGCTGGCCCACCTTGATGTGCGTCG
CGTTGTACCTGCGGGCGAAGATGCGGTCCATGGCGTCGCGGGCGTCCTTGCCGATGCAGTCCCCCAGGTCCACGC
GCGAGAGCGGGTACTCGGTCAGGTTGGTGGTGAAGGTGGTGGATATGGCGTCGGAAGAGAATCGGAAGGAGCCGC
CGTACTCGGAGCGCAGCATCTCGTCCACCTCCTGCCACTTGGTCATGGTGCAGACCGACGGGCGCTTTGGCACCC
AGTCCCAGGCCACGGTGAACTTGGGGGTCGTGAGCAGGTTCCGGGTGGTCGGCGCCGTGGCCCGGGCCTTGGTGG
TGAGGTCGCGCGCGTAGAAGCCGTCGACCTGCTTGAAGCGGTCGGCGGCGTAGCTGGTGTGTTCGGTGTGCGACC
CCTCCCGGTAGCCGTAAAACGGGGACATGTACACAAAGTCGCCAGTCGCCAACACAAACTCGTCGTACGGGTACA
CCGAGCGCGCGTCCACCTCCTCGACGATGCAGTTTACCGTCGTCCCGTACCGGTGGAACGCCTCCACCCGCGAGG
GGTTGTACTTGAGGTCGGTGGTGTGCCAGCCCCGGCTCGTGCGGGTCGCGGCGTTGGCCGGTTTCAGCTCCATGT
CGGTCTCGTGGTCGTCCCGGTGAAACGCGGTGGTCTCCAGGTTGTTGCGCACGTACTTGGCCGTGGACCGACAGA
CCCCCTTGGCGTTGATCTTGTCGATCACCTCCTCGAAGGGGACGGGGGCGCGGTCCTCAAAGATCCCCATAAACT
GGGAGTAGCGGTGGCCGAACCACACCTGCGAAACGGTGACGTCTTTGTAGTACATGGTGGCCTTGAACTTGTACG
GGGCGATGTTCTCCTTGAAGACCACCGCGATGCCCTCCGTGTAGTTCTGACCCTCGGGCCGGGTCGGGCAGCGGC
GCGGCTGCTCGAACTGCACCACCGTGGCGCCCGTGGGGGGTGGGCACACGTAAAAGTTTGCATCGGTGTTCTCCG
CCTTGATGTCCCGCAGGTGCTCGCGCAGGGTGGCGTGGCCCGCGGCGACGGTCGCGTTGTCGCCGGCGGGCGCG
GCGGCTTTGGGGGTTTCGGTTTTCTGTTCTTCTTCGGTTTCGGGTCCCCGTTGGGGGGCGCCAGGGGCGGGCG
GCGCCGGAGTGGCAGGGCCCCGTTCGCCGCCTGGGTCGCGGCCGCGACCCCAGGCGTGCCGGGGGAACTCGGAG
CCGCCGACGCCACCAGGACCCCCAGCGTCAACCCCAAGAGCGCCCATACGACGAACCACCGGCGCCCCGCGCGG
GGGCGCCCTGGCGCAT
```

FIG.2

```
5    CTTAGAGCTCGTCTTCGTCTCCGGCCTCGTCCTCGTTGTGGAGCGGAGAGTACCTGGCTTTGTTGCGCTTGCGCA
     GAACCATGTTGGTGACCTTGGAGCTGAGCAGGGCGCTCGTGCCCTTCTTTCTGGCCTTGTGTTCCGTGCGCTCCA
     TGGCCGACACCAAAGCCATATATCGGATCATTTCTCGGGCCTCGGCCAACTTGGCCTCGTCAAACCCGCCCCCCT
10   CCGCGCCTTCCTCCCCCTCCCCGCCCACGCCCCGGGGTCGGAAGTCTTGAGTTCCTTGGTGGTGAGCGGATACA
     GGGCCTTCATGGGATTGCGTTGCAGTTGCAGGACGTAGCGGAAGGCGAAGAAGGCCGCGACCAGGCCGGCCAGGA
     CCAGCAGCCCCACGGCAAGCGCCCCGAAGGGGTTGGACATAAAGGAGGACACGCCCGAGACGGCCGACACCACGC
     CCCCCACTACTCCCATGACTACCTTGCCGACCGCGCGCCCCAAGTCCCCCATCCCCTCGAAGAACGCGCACAGCC
     CCGCGAACATGGCGGCGTTGGCGTCGGCGGATGACCGTGTCGATGTCGGCAAAGCGCAGGTCGTGCAGCTGGT
15   TGCGGCGCTGGACCTCCGTGTAGTCCAGCAGGCCGCTGTCCTTGATCTCGTGGCGCGTGTAGACCTCCAGGGGCA
     CAAACTCGTGGTCCTCCAGCATGGTGATGTTCAGGTCGATGAAGGTGCTGACGGTGGTGACGTCGGCGCGACTCA
     GCTGGTGAGAGTACGCGTACTCCTCGAAGTACACGTAGCCCCCGCCGAAGATGAAGTAGCGCCGGTGGCCCACGG
     TGCACGGCTCGAGCGCGTCGCGGGTGAGGCGCAGCTCGTTGTTCTCGCCCAGCTGCCCCTCGATCAGCGGGCCCT
     GGTCTTCGTACCGAAAGCTGACCAGGGGGCGGCTGTAGCACGTCCCCGGCCGCGAGCTGACGCGCATCGAGTTCT
20   GCACGATCACGTTGTCCGGGGCGACGGGCACGCACGTGGAGACGGCCATGACGTCTCCGAGCATGCGCGCGCTCA
     CCCGCCGGCCGACGGTGGCGGAGGCGATGGCGTTGGGGTTGAGCTTGCGGGCCTCGTTCCAGAGAGTCAGCTCGT
     GGTTCTGCAGCTCGCACCACGCGACGGCGATGCGCCCAGCATGTCATTCACGTGGCGCTGTATGTGGTTATACG
     TAAACTGCAGCCGGGCGAACTCGATCGAGGAGGTGGTCTTGATGCGCTCCACGGACGCGTTGGCGCTGGGCGCCT
     CCCGCAGTGGCGCGGGCGTGGCATTCCGGGGCTTGCGGTCCTGCTCCCGCATGTACTCCCGCACGTACAGCTCGG
25   CGAGCGTGTTGCTGAGGAGGGGCTGGTACGCGATGAGGAAGCCCCCCGTGGCCAGGTAGTACTGCGGCTGGCCCA
     CCTTGATGTGCGTGGCGTTGTACTTGCGCGCAAACATGCGGTCGATGGCCTCGCGGGCATCCCGGCCGATGCAGT
     CGCCCAGGTCGACGCGCGAGAGCGAGTACTCGGTCAGGTTGGTGGTGAAGGTGGTCGAGATGGCGTCGGAGGAGA
     AGCGGAAGGAGCCGCCGTACTCGGCGCGGAGCATCTCGTCCACCTCCTGCCACTTGGTCATGGTGCAGACCGCCG
     GTCGCTTCGGCACCCAGTCCCAGGCCACGGTAAACTTGGGGGTCGTCAGCAAGTTGCGGGTCGTCGGCGACGTGG
30   CCCGGGCCTTCGTGGTGAGGTCGCGCGCGTAGAAGCCGTCGACCTGCTTGAAGCGGTCGGCGGCGTAGCTGGTGT
     GCTCGGTGTGCGACCCCTCCCGGTAGCCGTAAAACGGGGACATGTACACAAAGTCGCCCGTCGCCAGCACAAACT
     CATCGTACGGGTACACCGACCGCGCGTCCACCTCCTCGACGATGCAGTTGACCGTCGTGCCGTACCGATGGAACG
     CCTCCACCCGCGAGGGGTTGTACTTGAGGTCGGTGGTGTGCCACCCCCGGCTCGTGCGCGTGGCGACCTTCGCCG
     GCTTGAGCTCCATGTCGGTCTCGTGGTCGTCCCGGTGAAACGCGGTGGTCTCCATGTTGTTCCGCACGTACTTGG
35   CCGTGGAGCGGCAGACCCCCTTGGTGTTAATCTTGTCGATCACCTCCTCGAAGGGAACGGGGGCGCGGTCCTCGA
     ATATCCCCATAAACTGGGAGTAGCGGTGGCCGAACCACACCTGCGACACGGTCACGTCTTTGTAGTACATGGTGG
     CCTTGAATTTGTACGGGCGATGTTCTCCTTGAAGACCACCGCGATGCCCTCCGTGTAGTTCTGCCCCTCCGGGC
     GCGTCGGGCAGCGGCGCGGCTGCTCAAACTGCACCACCGTGGCGCCCGTCGGGGGCGGGCACACGTAAAACTGGG
     CATCGGCGTTCTCGACCTTGATTTCCCGCAGGTGCGCGCGCAGCGTGGCGTGGCCGGCGGCGACGGTCGCGTTGG
40   CGTCGGGGGCGGGGTCGCCTCGGGCCGCTTGGGCGGCTTTTTGGTTTTCCGCTTCCGGGCCTTGGTGGTCGCGG
     GGCTCGGGACGGGGGCGGCCGGGAGGCGGGACCCCCGTTCGCCGCGACGGTCGCGGCCACGCCGCCCGAGGCGC
     GGGGGGCCGCCGGGGCCGCCGGGGCCGCCGACGCCACCGCGGCCACCAGCGCCCCACGACCAGCGCGCAAATCA
     AGCCCCCCCGCGCAT
```

FIG.3

```
ATGCGCCAGGGCGCCCCCGCGCGGGGGCGCCGGTGGTTCGTCGTATGGGCGCTCTTGGGGTTGACGCTGG
GGGTCCTGGTGGCGTCGGCGGCTCCGAGTTCCCCCGGCACGCCTGGGGTCGCGGCCGCGACCCAGGCGGC
GAACGGGGGCCCTGCCACTCCGGCGCCGCCCGCCCCTGGCGCCCCCCAACGGGGGACCCGAAACCGAAG
AAGAACAGAAAACCGAAACCCCCAAAGCCGCCGCGCCCCGCCGGCGACAACGCGACCGTCGCCGCGGGCC
ACGCCACCCTGCGCGAGCACCTGCGGGACATCAAGGCGGAGAACACCGATGCAAACTTTTACGTGTGCCC
ACCCCCCACGGGCGCCACGGTGGTGCAGTTCGAGCAGCCGCGCCGCTGCCCGACCCGGCCCGAGGGTCAG
AACTACACGGAGGGCATCGCGGTGGTCTTCAAGGAGAACATCGCCCCGTACAAGTTCAAGGCCACCATGT
ACTACAAAGACGTCACCGTTTCGCAGGTGTGGTTCGGCCACCGCTACTCCCAGTTTATGGGGATCTTTGA
GGACCGCGCCCCCGTCCCCTTCGAGGAGGTGATCGACAAGATCAACGCCAAGGGGGTCTGTCGGTCCACG
GCCAAGTACGTGCGCAACAACCTGGAGACCACCGCGTTTCACCGGGACGACCACGAGACCGACATGGAGC
TGAAACCGGCCAACGCCGCGACCCGCACGAGCCGGGGCTGGCACACCACCGACCTCAAGTACAACCCCTC
GCGGGTGGAGGCGTTCCACCGGTACGGGACGACGGTAAACTGCATCGTCGAGGAGGTGGACGCGCGCTCG
GTGTACCCGTACGACGAGTTTGTGTTGGCGACTGGCGACTTTGTGTACATGTCCCCGTTTTACGGCTACC
GGGAGGGGTCGCACACCGAACACACCAGCTACGCCGCCGACCGCTTCAAGCAGGTCGACGGCTTCTACGC
GCGCGACCTCACCACCAAGGCCCGGGCCACGGCGCCGACCACCCGGAACCTGCTCACGACCCCCAAGTTC
ACCGTGGCCTGGGACTGGGTGCCAAAGCGCCCGTCGGTCTGCACCATGACCAAGTGGCAGGAGGTGGACG
AGATGCTGCGCTCCGAGTACGGCGGCTCCTTCCGATTCTCTTCCGACGCCATATCCACCACCTTCACCAC
CAACCTGACCGAGTACCCGCTCTCGCGCGTGGACCTGGGGGACTGCATCGGCAAGGACGCCCGCGACGCC
ATGGACCGCATCTTCGCCCGCAGGTACAACGCGACGCACATCAAGGTGGGCCAGCCGCAGTACTACCTGG
CCAATGGGGGCTTTCTGATCGCGTACCAGCCCCTTCTCAGCAACACGCTCGCGGAGCTGTACGTGCGGGA
ACACCTCCGCGAGCAGAGCCGCAAGCCCCCAAAACCCCACGCCCCCGCCGCCCGGGGCCAGCGCCAACGCG
TCCGTGGAGCGCATCAAGACCACCTCCTCCATCGAGTTCGCCAGGCTGCAGTTTACGTACAACCACATAC
AGCGCCATGTCAACGATATGTTGGGCCGCGTTGCCATCGCGTGGTGCGAGCTGCAGAATCACGAGCTGAC
CCTGTGGAACGAGGCCCGCAAGCTGAACCCCAACGCCATCGCCTCGGCCACCGTGGGCCGGCGGGTGAGC
GCGCGGATGCTCGGCGACGTGATGGCCGTCTCCACGTGCGTGCCGGTCGCCGCGGACAACGTGATCGTCC
AAAACTCGATGCGCATCAGCTCGCGGCCCGGGGCCTGCTACAGCCGCCCCCTGGTCAGCTTTCGGTACGA
AGACCAGGGCCCGTTGGTCGAGGGGCAGCTGGGGGGAGAACAACGAGCTGCGGCTGACGCGCGATGCGATC
GAGCCGTGCACCGTGGGACACCGGCGCTACTTCACCTTCGGTGGGGGCTACGTGTACTTCGAGGAGTACG
CGTACTCCCACCAGCTGAGCCGCGCCGACATCACCACCGTCAGCACCTTCATCGACCTCAACATCACCAT
GCTGGAGGATCACGAGTTTGTCCCCCTGGAGGTGTACACCCGCCACGAGATCAAGGACAGCGGCCTGCTG
GACTACACGGAGGTCCAGCGCCGCAACCAGCTGCACGACCTGCGCTTCGCCGACATCGACACGGTCATCC
ACGCCGACGCCAACGCCGCCATGTTTGCGGGCCTGGGCGCGTTCTTCGAGGGGATGGGCGACCTGGGGCG
CGCGGTCGGCAAGGTGGTCATGGGCATCGTGGGCGGCGTGGTATCGGCCGTGTCGGGCGTGTCCTCCTTC
ATGTCCAACCCCTTTGGGGCGCTGGCCGTGGGTCTGTTGGTCCTGGCCGGCCTGGCGGCGGCCTTCTTCG
CCTTTCGCTACGTCATGCGGCTGCAGAGCAACCCCATGAAGGCCCTGTACCCGCTAACCACCAAGGAGCT
CAAGAACCCCACCAACCCGGACGCGTCCGGGGAGGGCGAGGAGGGCGGCGACTTTGACGAGGCCAAGCTA
GCCGAGGCCCGGGAGATGATACGGTACATGGCCCTGGTGTCTGCCATGGAGCGCACGGAACACAAGGCCA
GAAGGAAGGGCACGAGCGCGCTGCTCAGCGCCAAGGTCACCGACATGGTCATGCGCAAGCGCCGCAACAC
CAACTACACCCAAGTTCCCAACAAAGACGGTGACGCCGACGAGGACGACCTGTGAT
```

FIG.4

```
ATGCGCGGGGGGGGCTTGATTTGCGCGCTGGTCGTGGGGGCGCTGGTGGCCGCGGTGGCGTCGGCGGCCC
CGGCGGCCCCGGCGGCCCCCCGCGCCTCGGGCGGCGTGGCCGCGACCGTCGCGGCGAACGGGGGTCCCGC
CTCCCGGCCGCCCCCCGTCCCGAGCCCCGCGACCACCAAGGCCCGGAAGCGGAAAACCAAAAAGCCGCCC
AAGCGGCCCGAGGCGACCCCGCCCCCCGACGCCAACGCGACCGTCGCCGCCGGCCACGCCACGCTGCGCG
CGCACCTGCGGGAAATCAAGGTCGAGAACGCCGATGCCCAGTTTTACGTGTGCCCGCCCCCGACGGGCGC
CACGGTGGTGCAGTTTGAGCAGCCGCGCCGCTGCCCGACGCGCCCGGAGGGGCAGAACTACACGGAGGGC
ATCGCGGTGGTCTTCAAGGAGAACATCGCCCCGTACAAATTCAAGGCCACCATGTACTACAAAGACGTGA
CCGTGTCGCAGGTGTGGTTCGGCCACCGCTACTCCCAGTTTATGGGGATATTCGAGGACCGCGCCCCCGT
TCCCTTCGAGGAGGTGATCGACAAGATTAACACCAAGGGGGTCTGCCGCTCCACGGCCAAGTACGTGCGG
AACAACATGGAGACCACCGCGTTTCACCGGGACGACCACGAGACCGACATGGAGCTCAAGCCGGCGAAGG
TCGCCACGCGCACGAGCCGGGGGTGGCACACCACCGACCTCAAGTACAACCCCTCGCGGGTGGAGGCGTT
CCATCGGTACGGCACGACGGTCAACTGCATCGTCGAGGAGGTGGACGCGCGGTCGGTGTACCCGTACGAT
GAGTTTGTGCTGGCGACGGGCGACTTTGTGTACATGTCCCCGTTTTACGGCTACCGGGAGGGGTCGCACA
CCGAGCACACCAGCTACGCCGCCGACCGCTTCAAGCAGGTCGACGGCTTCTACGCGCGCGACCTCACCAC
GAAGGCCCGGGCCACGTCGCCGACGACCCGCAACTTGCTGACGACCCCCAAGTTTACCGTGGCCTGGGAC
TGGGTGCCGAAGCGACCGGCGGTCTGCACCATGACCAAGTGGCAGGAGGTGGACGAGATGCTCCGCGCCG
AGTACGGCGGCTCCTTCCGCTTCTCCTCCGACGCCATCTCGACCACCTTCACCACCAACCTGACCGAGTA
CTCGCTCTCGCGCGTCGACCTGGGCGACTGCATCGGCCGGGATGCCCGCGAGGCCATCGACCGCATGTTT
GCGCGCAAGTACAACGCCACGCACATCAAGGTGGGCCAGCCGCAGTACTACCTGGCCACGGGGGGCTTCC
TCATCGCGTACCAGCCCTCCTCAGCAACACGCTCGCCGAGCTGTACGTGCGGGAGTACATGCGGGAGCA
GGACCGCAAGCCCCGGAATGCCACGCCCGCGCCACTGCGGGAGGCGCCCAGCGCCAACGCGTCCGTGGAG
CGCATCAAGACCACCTCCTCGATCGAGTTCGCCCGGCTGCAGTTTACGTATAACCACATACAGCGCCACG
TGAATGACATGCTGGGGCGCATCGCCGTCGCGTGGTGCGAGCTGCAGAACCACGAGCTGACTCTCTGGAA
CGAGGCCCGCAAGCTCAACCCCAACGCCATCGCCTCCGCCACCGTCGGCCGGCGGGTGAGCGCGCGCATG
CTCGGAGACGTCATGGCCGTCTCCACGTGCGTGCCCGTCGCCCCGGACAACGTGATCGTGCAGAACTCGA
TGCGCGTCAGCTCGCGGCCGGGGACGTGCTACAGCCGCCCCTGGTCAGCTTTCGGTACGAAGACCAGGG
CCCGCTGATCGAGGGGCAGCTGGGCGAGAACAACGAGCTGCGCCTCACCCGCGACGCGCTCGAGCCGTGC
ACCGTGGGCCACCGGCGCTACTTCATCTTCGGCGGGGCTACGTGTACTTCGAGGAGTACGCGTACTCTC
ACCAGCTGAGTCGCGCCGACGTCACCACCGTCAGCACCTTCATCGACCTGAACATCACCATGCTGGAGGA
CCACGAGTTTGTGCCCCTGGAGGTCTACACGCGCCACGAGATCAAGGACAGCGGCCTGCTGGACTACACG
GAGGTCCAGCGCCGCAACCAGCTGCACGACCTGCGCTTTGCCGACATCGACACGGTCATCCGCGCCGACG
CCAACGCCGCCATGTTCGCGGGGCTGTGCGCGTTCTTCGAGGGGATGGGGGACTTGGGGCGCGCGGTCGG
CAAGGTAGTCATGGGAGTAGTGGGGGGCGTGGTGTCGGCCGTCTCGGGCGTGTCCTCCTTTATGTCCAAC
CCCTTCGGGGCGCTTGCCGTGGGGCTGCTGGTCCTGGCCGGCCTGGTCGCGGCCTTCTTCGCCTTCCGCT
ACGTCCTGCAACTGCAACGCAATCCCATGAAGGCCCTGTATCCGCTCACCACCAAGGAACTCAAGACTTC
CGACCCCGGGGGCGTGGGCGGGGAGGGGGAGGAAGGCGCGGAGGGGGGCGGGTTTGACGAGGCCAAGTTG
GCCGAGGCCCGAGAAATGATCCGATATATGGCTTTGGTGTCGGCCATGGAGCGCACGGAACACAAGGCCA
GAAAGAAGGGCACGAGCGCCCTGCTCAGCTCCAAGGTCACCAACATGGTTCTGCGCAAGCGCAACAAAGC
CAGGTACTCTCCGCTCCACAACGAGGACGAGGCCGGAGACGAAGACGAGCTCTAAG
```

METHODS AND COMPOSITIONS RELATED THERETO FOR DETECTING AND IDENTIFYING DISTINCT SPECIES OF NUCLEIC ACIDS FROM CAUSATIVE AGENTS

CROSS-REFERENCE TO RELATED APPLICATIONS

The present application is a continuation of U.S. application Ser. No. 11/246,976, filed Oct. 7, 2005, now U.S. Pat. No. 8,030,032, which claims the benefit of priority under 35 U.S.C. §119(e) to U.S. Provisional Application No. 60/616,723, filed Oct. 7, 2004, the entire disclosure of which is hereby incorporated by reference in its entirety.

FIELD OF THE INVENTION

The present invention relates to methods for ascertaining whether a sample includes a first nucleic acid-containing entity or a second nucleic acid-containing entity particularly in the field of clinical diagnostic services, i.e., in the industry of the detection and identification of biological agents associated with disease conditions.

BACKGROUND OF THE INVENTION

Clinical diagnostics provide an essential aid to the physician for the diagnosis and monitoring of numerous pathologies and infectious diseases. Rapid and accurate identification of causative agents of a myriad of different human pathophysiological conditions is a paramount requisite to effective treatment.

A biological sample generally is taken from the patient, most often at the request of a physician, and sent to a medical laboratory for analysis to establish or confirm a diagnosis of clinical symptoms. A physician may suspect a particular causative agent upon physical examination. However, certain symptoms may be characteristic of a plethora of different causative agents. Therefore, due to misdiagnoses of causative agents, patients may be treated non-efficaciously. Moreover, in other instances, a physician may request a certain diagnostic test to be performed on a clinical specimen wherein the test subsequently produces a negative result. Then, of course, further clinical samples and diagnostic testing is required. In many instances, due to the lack of timely and accurate diagnoses, patients' original conditions progress to the further detriment of treatability and to the well-being of the patient. Accurate clinical diagnosis is critical to specifically identify causative agents, and in many cases specific species of infectious agents which mediate pathophysiological conditions in a timely manner. Accordingly, a need indeed exists for methods for detecting and identifying distinct species, in a single container, from a genus of infectious agents.

Direct detection techniques for Herpes Simplex Virus (HSV), for example, can include viral culture, Tzanck's smear, antigen detection, direct fluorescent antibody analysis, and viral DNA detection. Cusini et al., 2001, J. Antimicrob. Chemother. 47 Suppl T1, 9-16.

The use of conventional PCR techniques with probe-based hybridization for the direct detection of HSV DNA have been reported for subtyping of clinical specimens. Cone et al., 1991, J. Infect. Dis. 164:757-60. Conventional PCR has significant advantages over viral culture procedures, as the virus does not have to be infective and HSV DNA can be detected in the late stages of genital lesions more efficiently. Lucotte et al., 1995, Mol. Cell Probes 9:287-90. Stocher et al. reported on the parallel detection of CMV, EBV, HSV-1, HSV-2, and VZV from cerebrospinal fluid, serum, and plasma samples utilizing the LightCycler real-time PCR technology. Stocher et al., 2003, J. Clin. Virol. 26:85-93. Two reports developed TaqMan assays for the parallel detection of members of the Herpesviridae family in multiple, separate assays and yet another two have reported on SYBR green real-time PCR assays for the parallel detection of HSV-1, HSV-2, or both in clinical specimens. van Doornum et al., 2003, J. Clin. Microbiol. 41:576-80; Weidmann et al., 2003, J. Clin. Microbiol. 41:1565-8; Nicoll et al., 2001, J. Virol. Methods 96:25-31; Schmutzhard et al., 2004, J. Clin. Virol. 29:120-6. A recent study, for example, was published which analyzed the presence of HSV in more than 36,000 mucosal secretions found the detection rate of HSV DNA by real-time PCR techniques to be 12.1% of the samples versus 3.0% detected by viral culture. The method employed, however, could not discriminate between HSV-1 and HSV-2. Wald et al., 2003, J. Infect Dis. 188:1345-51.

Particularly, the need exists in the industry for rapid and accurate methods for ascertaining whether a sample includes a first nucleic acid-containing entity or a second nucleic acid-containing entity, the ability, for example, to identify distinct species of nucleic acids corresponding to distinct species of infectious agents in a single container.

SUMMARY OF THE INVENTION

The present invention is directed to methods for ascertaining whether a sample includes a first nucleic acid-containing entity or a second nucleic acid-containing entity, comprising (a) providing a single vessel containing (1) a nucleic acid from the sample, (2) a forward primer, (3) a reverse primer, (4) a first probe specific to the first entity, and (5) a second probe specific to the second entity, wherein a combination comprising the forward primer and the reverse primer is capable of amplifying, by the polymerase chain reaction, a segment of the nucleic acid of (1) the first entity to produce a first amplicon, and (2) the second entity to produce a second amplicon, and wherein the nucleotide sequence of the first amplicon and the nucleotide sequence of the second amplicon are not identical, (b) incubating the vessel under conditions allowing production of (1) the first amplicon if the sample contains the first entity, and (2) the second amplicon if the sample contains the second entity, (c) detecting a first signal generated from the first probe if the first amplicon is produced in (b), and detecting a second signal generated from the second probe if the second amplicon is produced in (b), and (d) ascertaining that (1) the sample does not contain the first entity or the second entity if the first signal and the second signal are not detected in (c), (2) the sample contains the first entity and does not contain the second entity if the first signal is detected in (c) and the second signal is not detected in (c), (3) the sample does not contain the first entity and contains the second entity if the first signal is not detected in (c) and the second signal is detected in (c), or (4) the sample contains the first entity and the second entity if the first signal and the second signal are detected in (c).

In addition, the current invention is directed to methods for ascertaining whether a sample includes a first nucleic acid-containing entity or a second nucleic acid-containing entity wherein both the first nucleic acid-containing entity and a second nucleic acid-containing entity are members of the Herpesviridae family.

The invention is further directed to methods wherein the first entity is HSV-1, and wherein the second entity is HSV-2, for example, wherein the first amplicon and the second amplicon contain at least a segment of the open reading frame of a gene encoding a glycoprotein, e.g., glycoprotein B.

Further, the invention is directed to compositions for the detection and distinct identification of HSV-1 and HSV-2 comprising a first oligonucleotide primer, at least 8 nucleotides in length, common to a region within positions 978 to 1149 (5-3') of SEQ ID NO:2 and the corresponding homolog region of SEQ ID NO:1 and, a second oligonucleotide primer, at least 8 nucleotides in length, that is common to a region within positions 1348 to 1546 (5-3') of SEQ ID NO:3 and the corresponding homolog region of SEQ ID NO:4., and a first oligonucleotide probe between about 15 and about 40 nucleotides in length specific to a sequence selected from the group consisting of SEQ ID NO:1 and SEQ ID NO:3 and a second oligonucleotide probe between about 15 and about 40 nucleotides in length specific to a sequence selected from the group consisting of SEQ ID NO:2 and SEQ ID NO:4, wherein the first and second oligonucleotide probes are each detectably labeled with distinctly different detectable labels.

BRIEF DESCRIPTION OF THE FIGURES

FIG. 1 displays SEQ ID NO:1 (reverse complement of HSV-1 coding region for glycoprotein B), an example distinct species of nucleic acid from a certain genus of infectious agents (HSV-1 and HSV-2).

FIG. 2 displays SEQ ID NO:2 (reverse complement of HSV-2 coding region for glycoprotein B), an example distinct species of nucleic acid from a certain genus of infectious agents (HSV-1 and HSV-2).

FIG. 3 displays SEQ ID NO:3 (HSV-1 coding region for glycoprotein B), an example distinct species of nucleic acid from a certain genus of infectious agents (HSV-1 and HSV-2).

FIG. 4 displays SEQ ID NO:4 (HSV-2 coding region for glycoprotein B), an example distinct species of nucleic acid from a certain genus of infectious agents (HSV-1 and HSV-2).

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Physicians are generally faced with observing patients' symptoms, obtaining biological samples, and ordering clinical diagnostic tests to determine the identity of causative agents which mediate pathological conditions. Since methods of treatment of pathophysiological conditions are intimately related to the species of the causative agent(s) of the condition, rapid and accurate identification and reporting of the species of causative agent(s) is of paramount importance in many cases to the practice of medicine today. The present invention enables the accurate and rapid detection and identification of distinct species of nucleic acids from a genus of causative agents derived from each clinical sample.

An embodiment of the present invention, for example, is a method for ascertaining whether a sample includes a first nucleic acid-containing entity or a second nucleic acid-containing entity, wherein the method comprises, (a) providing a single vessel containing (1) a nucleic acid from the sample, (2) a forward primer, (3) a reverse primer, (4) a first probe specific to the first entity, and (5) a second probe specific to the second entity, wherein a combination comprising the forward primer and the reverse primer is capable of amplifying, by the polymerase chain reaction, a segment of the nucleic acid of (1) the first entity to produce a first amplicon, and (2) the second entity to produce a second amplicon, and wherein the nucleotide sequence of the first amplicon and the nucleotide sequence of the second amplicon are not identical, (b) incubating the vessel under conditions allowing production of (1) the first amplicon if the sample contains the first entity, and (2) the second amplicon if the sample contains the second entity, (c) detecting a first signal generated from the first probe if the first amplicon is produced in (b), and detecting a second signal generated from the second probe if the second amplicon is produced in (b), and (d) ascertaining that (1) the sample does not contain the first entity or the second entity if the first signal and the second signal are not detected in (c), (2) the sample contains the first entity and does not contain the second entity if the first signal is detected in (c) and the second signal is not detected in (c), (3) the sample does not contain the first entity and contains the second entity if the first signal is not detected in (c) and the second signal is detected in (c), or (4) the sample contains the first entity and the second entity if the first signal and the second signal are detected in (c).

Exemplary methods are wherein the first entity is a first strain of a herpesvirus (i.e., a member of the Herpesviridae family), and wherein the second entity is a second strain of a herpesvirus. For example, wherein the first entity is HSV-1, and wherein the second entity is HSV-2.

The present invention includes but is not limited to PCR methods as well as primers and probes for detecting and specifically identifying and discriminating the presence of HSV-1 and HSV-2 in a sample in a single tube reaction, for example.

Exemplified herein is the design and validation of an example real-time PCR assay capable of simultaneously detecting each HSV subtype. Particularly, methods of the present invention are provided for detecting and specifically identifying and discriminating the presence of HSV-1 and HSV-2 in a sample in a single tube reaction. The methods are applied, for example, in the detection of HSV-1 and/or HSV-2 in a biological sample from a patient. An example presented herein particularly employ a pair of PCR amplification primers wherein each primer is homologous to a glycoprotein B coding region of both HSV-1 and HSV-2 but which also flank and thereby target divergent sequences in the viral subtypes for amplification. Separate probes are employed which correspond to distinct HSV-1 and HSV-2 nucleic acid sequences within the divergent amplified regions. Accordingly, example reagents, i.e., primers and probes are provided. Separate labels and separate quenchers, discussed infra, are employed in connection with each of the probes in the example presented herein. Real-time methods are preferred embodiments of the present invention. Methods of the invention are a significantly more sensitive clinical diagnostic technique capable of detecting and specifically identifying and discriminating the presence of HSV-1 and HSV-2, for example, in a single reaction tube while providing accurate results in a fraction of the time of viral culture and conventional PCR methods.

The example described herein validated an example combination of primers and dual-labeled oligonucleotide probes for the type-specific detection of HSV DNA in a single reaction.

Exemplary Illustration of an Embodiment of the Invention

One embodiment of the present invention is a multiplex real-time PCR assay developed to simultaneously detect HSV-1 and/or HSV-2 on a Rotor-Gene 3000 platform, for example. Subtyping validation in this example was performed by Pyrosequencing to obtain short sequences of nucleotides capable of identifying HSV-1 and/or HSV-2 DNA. This technique was applied to 4,581 cervicovaginal swabs sampled from women primarily from six states. The prevalence of HSV detection in these specimens is presented to illustrate an example application of the general methods of the present invention.

Confirmed positive HSV-1 and HSV-2 samples purchased from the American Type Culture Collection (ATCC) and HSV-1 and HSV-2 infected clinical specimens were assayed simultaneously with shared amplification primers and subtype-specific probes against the HSV glycoprotein B gene on a Rotor-Gene 3000 platform. A distinct set of primers towards heterogeneous genes of HSV was avoided to minimize cross-reactivities, which could be inherent to the incorporation of four oligonucleotide primers and two dual-labeled probes into a single reaction. Separately, two PCR reactions were performed in which one primer contained a 5' biotinylated modification. Single-stranded DNA from the amplicon was purified and Pyrosequenced.

The quantitative range of the assay extended from $10^8$ through 10 copies of each virus ($r^2 > 0.991$) and specificity was determined by non-amplification of 37 different human pathogens, including other herpesviruses such as VZV, CMV, and EBV. Sensitivity and specificity values of 100% were calculated by concordance analysis between the real-time PCR and the DNA Pyrosequencing results (HSV-1: n=119, HSV-2: n=120). Application of this assay to 4,581 cervicovaginal swab specimens collected from women visiting physicians primarily in six states provided detection rates of 3.1% for HSV-1 and 7.6% for HSV-2. The average age of women infected with HSV-1 was 29.5 versus 35.6 for HSV-2. Of the 4,581 cervical swab DNA specimens analyzed for the presence of HSV-1 or HSV-2 DNA by this testing procedure, 479 (10.5%, 95% CI, 9.61-11.4%) were determined to be positive for either subtype. This compared to 1,779 of 10,974 positive HSV specimens (16.2%; 95% CI, 15.5-16.9%) collected in the Puget Sound area in Washington and 24% and 36% of 110 clinical dermal or genital lesion specimens from patients with suspected mucocutaneous HSV infections which were positive for HSV-1 and HSV-2, respectively, in another study in which the sequence-unspecific SYBR green dye was incorporated into a real-time PCR reaction. Wald et al., 2003, J. Infect. Dis. 188:1345-51; Schmutzhard et al., 2004, J. Clin. Virol 29:120-6. Of the 4,581 clinical cervical swab specimens analyzed, none were determined to simultaneously contain both HSV-1 and HSV-2. An analysis of the NHANES III data reported that 16.6% of the 13,904 American individuals tested were seropositive for both HSV-1 and HSV-2, although this statistic does not indicate if lesions indicative of infection from both viruses were present simultaneously. With respect to infection by both viral herpes subtypes, some studies have suggested an initial infection with HSV-1 reduces the likelihood that a subsequent HSV-2 infection will be symptomatic. Xu et al., 2002, J. Infect. Dis. 185:1019-24.

Real-time PCR is a proven advancement over conventional PCR as the decrease in turn-around time is even more pronounced as the need for time-consuming agarose gel separation techniques is obviated. Some platforms, like the Rotor-Gene 3000 used in this study, operate as a closed-tube system and coupled with enzymes like uracil-DNA glycosylase (UNG) can further reduce the possibility of carryover contamination. The example of the present invention presented herein is a real-time PCR assay which is both highly sensitive and specific for the simultaneous subtype-specific detection of both HSV-1 and HSV-2 DNA in a single reaction.

Pyrosequencing was utilized in an example embodiment presented herein as a rapid and innovative nucleic acid based sequencing solution for validating the identity of the HSV subtype in a clinical specimen. A heterogeneous region was sequenced to readily distinguish one subtype from another as an alternative to immunofluorescence screening of viral cultures with subtype-specific antisera. Pyrosequencing is amenable to a 96 well format permitting the simultaneous screening of a large number of specimens and is also rapid in that once a run is initiated, approximately one nucleotide can be dispensed per minute with real-time data acquisition and interpretation. When the Pyrosequencing analysis of clinical specimens was used as a standard, 100% sensitivity and specificity for both HSV-1 and HSV-2 were calculated. This validation procedure used in conjunction with the described real-time PCR exemplifies an embodiment of the present invention for the simultaneous direct molecular detection of both subtypes of HSV DNA.

Example HSV-1 and HSV-2 Primers and Probes

The oligonucleotide primers and probes specifically employed in a certain embodiment of the invention presented herein were synthesized by Integrated DNA Technologies (IDT, Coralville, Iowa) and are listed in Table I. The dual-labeled oligonucleotide probes and 5' biotinylated primers were purified by high performance liquid chromatography (HPLC) by the manufacturer.

TABLE II

Example Primer and probe sequences for real-time PCR amplification and detection of HSV-1 and HSV-2

| Primer | Sequence 5' to 3' |
|---|---|
| HSV1/2 FOR | TTCTGCAGCTCGCACCAC<br>(SEQ ID NO: 5) |
| HSV1/2 REV | GGAGCGCATCAAGACCACC<br>(SEQ ID NO: 6) |
| HSV1Pr | 6-carboxyfluorescein/CGATGGCAACGCGGCCCAACATATCGTTGAC<br>(SEQ ID NO: 7)/BHQ-1 |
| HSV2Pr | Cy5/CGATGCGCCCCAGCATGTCGTTCACGT<br>(SEQ ID NO: 8)/BHQ-2 |
|  | Cy5/CGATGCGCCCCAGCATGTCATTCACGT<br>(SEQ ID NO: 9)/BHQ-2 |

TABLE II-continued

Example Primer and probe sequences for real-time PCR amplification and detection of HSV-1 and HSV-2

| Primer | Sequence 5' to 3' |
|---|---|
| HSV2a-1 (Cone et al., 1991) | CTGGTCAGCTTTCGGTACGA (SEQ ID NO: 10) |
| HSV2a-2 (Cone et al., 1991) | CAGGTCGTGCAGCTGGTTGC (SEQ ID NO: 11) |
| HSVcv-seq1 | CCTTGATCTCGTGGC (SEQ ID NO: 12) |

Primers and probes (nucleic acid reagents) for employment in methods of the present invention are herein expressly not limited to those exemplified in Table I. The following discussion of example reagents for use in methods of the present invention particularly refers to FIG. 1 (SEQ ID NO:1), FIG. 2 (SEQ ID NO:2), FIG. 3 (SEQ ID NO:3), and FIG. 4 (SEQ ID NO:4) attached hereto, nucleic acids (positions 1-2716) HSV-1 and HSV-2 corresponding to respective regions of each subtype for glycoprotein B. See, e.g., NCBI accession Nos. X14112.1 and Z86099.2.

Primers

The "HSV1/2 FOR" (forward) primer (SEQ ID NO:5) exemplified in Table I, for example, is derived from a homolog portion of the reverse complement sequence of the HSV-1 and HSV-2 coding region for glycoprotein B that is common to both species (i.e., the homologous genes are identical in sequence at that site). The HSV-2 reverse complement of the coding region for glycoprotein B is shown in FIG. 2 (SEQ ID NO:2). SEQ ID NO:5 is the same as positions 1128-1145 of SEQ ID NO:2. The corresponding homologous region of the HSV-1 reverse complement of the coding region for glycoprotein B are positions 1119-1136 of SEQ ID NO: (FIG. 1). Accordingly, SEQ ID NO:5 is the same as positions 1119-1136 of SEQ ID NO: 1.

The "HSV 1/2 REV" (reverse) primer (SEQ ID NO:6) exemplified in Table I, for example, is derived from a homologous portion, i.e., 'common to' or identical in sequence, of the HSV-1 and HSV-2 coding region for glycoprotein B. The HSV-1 coding region for glycoprotein B is shown in FIG. 3 (SEQ ID NO:3). SEQ ID NO:6 is the same as positions 1476-1494 of SEQ ID NO:3. The corresponding homologous region of the HSV-2 coding region for glycoprotein B are positions 1467-1485 of SEQ ID NO:4 (FIG. 4). Accordingly, SEQ ID NO:6 is the same as positions 1467-1485 of SEQ ID NO:4.

Accordingly, example target regions of HSV-1 and HSV-2 nucleic acids, i.e., respective glycoprotein B regions, correspond to positions 1128 to about position 1250 of SEQ ID NO:2. This target region for amplification is therefore at least about 118-125 nucleotide bases in length, e.g., 122, nucleotides in length. Target regions of the present invention comprise, for example, positions 1131-1240 of SEQ ID NO:2. The art of selection and synthesis of PCR primers in order to amplify a particular target sequence is indeed well-known to those of ordinary skill in the art. Typically, oligonucleotide primers are about 8 to about 50 nucleotides in length (e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length). Primers 12 to 24 nucleotides in length are preferred. Primer pairs that amplify particular nucleic acid molecules, e.g., both HSV-1 and HSV-2 regions less than about 410 bases in length (preferably less than about 250 bases in length) that comprise, for example, or correspond to positions 1131-1240 of SEQ ID NO:2, can be designed using, for example, a computer program such as OLIGO (Molecular Biology Insights, Inc., Cascade, Colo.). Important features in choosing primers to target HSV-1 and HSV-2 regions of the present invention, for example, include that both the forward and reverse primers, although not necessary, per se, are preferably consensus, i.e., homologous (identical matches or exactly complementary in the case of reverse primers) to both HSV-1 and HSV-2 coding regions of glycoprotein B.

In addition to what is discussed supra, an important factor in the success of this embodiment of the present invention is that the primers function in PCR to amplify HSV-1 and HSV-2 regions less than about 410 bases in length that comprise, for example, positions 1131-1240 of SEQ ID NO:2. Accordingly, another HSV-1 and HSV-2 preferred target region of the present invention, for example, with reference to SEQ ID NO:2, for example, comprises a nucleic acid sequence which extends from about position 1011, 1010, 1009, 1008, 1007, 1006, 1005, 1003, or 1002 to about position 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, or 1269. Another HSV-1 and HSV-2 preferred target region of the present invention, for example, with reference to SEQ ID NO:2, comprises a nucleic acid sequence which extends from about position 980, 979 or 978 to about position 1380, 1381, 1382, 1383 or 1384. The Applicants point out, however, that primers corresponding to each of the 5' and 3' terminal portions of the various target regions of HSV-1 and HSV-2 target nucleic acids discussed herein may be combined with each other. Accordingly, all primers disclosed, suggested, and contemplated herein are each independently regarded as novel compositions of matter that can be employed pairwise to amplify HSV-1 and HSV-2 regions at least about 110 bases in length but less than about 410 bases in length that comprise, for example, the region corresponding to positions 1131-1240 of HSV-2 as indicated in SEQ ID NO:2.

Probes

Nucleic acid probes for use in methods of the present invention are preferably within the range of about 15 to about 50 nucleotides in length. More preferred probes are generally within the range of about 20 to about 40 nucleotides in length.

Particularly preferred probes for use in methods of the present invention comprise positions 1154 to 1169 of SEQ ID NO:2 or the complement thereof as well as a probe specific to the corresponding homolog region of SEQ ID NO:1 or an exact complement thereof. The "HSV1Pr" (HSV-1 probe) exemplified in Table I, for example, is derived from the target region of HSV-1 shown in SEQ ID NO:1 (positions 1138-1168) (corresponding to SEQ ID NO:2 homolog positions 1147-1173). Many different HSV-1 probes may be employed in methods of the present invention to selectively hybridize to the amplified HSV-1 target region. Derivative probes of the HSV-1 probe shown in Table I, for example, may be constructed by extending and/or truncating the exemplified species, in view of FIG. 1, at either/or both the 5' and 3' ends.

Example HSV-2 probes for use in methods of the present invention comprise SEQ ID NO:2 positions 1160 to 1175 of HSV-2 or homolog positions corresponding thereto. The "HSV2Pr" (HSV-2 probes) exemplified in Table I, for example, is derived from the target region of HSV-2 (SEQ ID NO:2), e.g., corresponding to positions 1153-1179. Many different HSV-2 probes may be employed in methods of the present invention to selectively hybridize to the amplified HSV-2 target region. Derivative probes of the HSV-2 probes shown in Table I, for example, may be constructed by extending and/or truncating the exemplified species, in view of SEQ ID NO:2, for example.

Detectable labels and quenchers indicated in Table I in association with the exemplified probes are readily substituted by any of a myriad of similar functional entities now well-known to those of ordinary skill in the art.

Real-Time PCR Amplification Parameters

Each 25 µl reaction contained 0.5 µg extracted DNA, 0.90 µM HSV1/2 FOR, 0.90 µM HSV1/2 REV, 0.2 µM HSV1Pr, 0.05 µM HSV2Pr, and 1× qPCR mastermix (Eurogentec, San Diego, Calif.) which contains dNTP/dUTP, Hot Goldstar DNA polymerase, $MgCl_2$, and uracil-DNA glycosylase (UNG). The real-time PCR reactions were performed on a Rotor-Gene 3000 instrument (Corbett Research, Mortlake, Australia) and included an initial incubation at 50° C. for 2 min for UNG activity followed by 95° C. for 10 min to inactivate the UNG, activate the Hot Goldstar DNA polymerase, and initially denature the DNA. Next, 35 cycles of denaturation (95° C., 15 sec) and annealing/extension (55° C., 45 sec) were performed with consecutive acquisition at 470 nm source/510 nm detection (HSV1Pr) and 625 nm source/660 hp detection (HSV2Pr) immediately following each annealing/extension step. Analysis was performed with the Rotor-Gene 3000 Software, Version 5 (Build 47) with slope correction and reaction efficiency threshold enabled and the negative template control (NTC) threshold set to a maximum of 10%. The amplification target for both viruses is the HSV glycoprotein B gene and successful amplification would result in a 122 bp product. Positive results from clinical specimens were confirmed by repeating the initial reaction in two separate reactions, each with a single dual-labeled probe and fluorescence acquisition tailored to the respective fluorophore.

Pyrosequencing

Pyrosequencing is a bioluminescent sequencing procedure permitting the identification of short oligonucleotide segments of DNA up to 100 nucleotides in length (Gharizadeh et al., 2002, Anal. Biochem. 301(1):82-90; Ronaghi et al., 1998, Science. 281(5375):363-5.). A Pyrosequencing procedure was used to identify PCR positive amplicons as either HSV-1 or HSV-2 for comparison with the subtype-specific real-time PCR reactions. For single-stranded DNA purification prior to Pyrosequencing analysis, the HSV1/2 Rev and HSV2a-1 primers were each synthesized with a 5' biotin label which was incorporated into the amplicon during the amplification process. The biotinylated PCR product was captured with streptavidin Sepharose and purified with a vacuum prep workstation according to the manufacturer's instructions (Biotage, Uppsala, Sweden). For the Pyrosequencing reaction, HSVcv-seq1 was utilized to prime the 5' biotin-HSV2a-1 and HSV-2a-2 amplification product and HSV1/2 FOR was used to sequence the 5' biotin-HSV1/2 REV and HSV1/2 FOR amplicons. A Pyrosequencing 96MA System was programmed with a directed nucleotide dispensation order of TGCGATCTGCGACTCG for the real-time PCR primers and 15 cycles of a repetitive ATCG dispensation order for amplicons derived from conventional PCR primer amplification. The resulting pyrograms were analyzed with the PSQ 96MA version 2.0.2 software.

Precautions Against Contamination

Extraction of DNA, preparation of the PCR reactions, amplification in the Rotor-Gene 3000 machines, and the Pyrosequencing procedures were each performed in physically separate rooms. Pyrogen-free, nuclease-free water was used in the isolation of DNA from the cervicovaginal swabs and ATCC extracted controls. New Finn pipettes were used solely with filter tips for PCR. PCRs were each prepared in a UV-irradiated PCR biohood and UNG was incorporated into the Eurogentec PCR mastermix to minimize, if not eliminate, the possibility of carry-over contamination (Poljak et al., 1998, J. Virol. Methods. 71(1):1-6.).

Statistical Analysis

Mean values are presented with standard deviations (SD). Two-sided 95% confidence intervals (95% CI) were calculated using the Wilson procedure (Newcombe, 1998. Stat. Med. 17(8).857-72.). All calculations were performed using Microsoft Excel v.X, VassarStats (Lowry, 1998-2002, 2004: www.vassarstats.com), and GraphPad Instat version 3.0b for Macintosh (GraphPad Software, San Diego, Calif.).

Sensitivity

For each HSV target, a positive vector control was generated as described in Example III. Spectrophotometric analysis was utilized to determine the plasmid concentration and serial dilutions from $1\times10^8$ through 10 copies of each vector were added as template in triplicate. Fluorescent signal acquisition was performed consecutively during the same reaction in two different channels, 6-carboxyfluorescein for HSV-1 (HSV1Pr probe) and Cy5 for HSV-2 (HSV2Pr probe). Linear regression analysis of the cycle threshold ($C_T$) values demonstrating the quantitative capacity of the assay; $r^2$ values of 0.991 and 0.999 were calculated for the HSV-1 and HSV-2 probes, respectively. One observation with this assay was a quantitative inability to detect a signal from one HSV type when the other subtype is present in the same reaction by a difference of three orders of magnitude or more. If both were present in concentrations that differed by less than this, either at high or low quantities, the detection capacity was unaffected.

Specificity

NCBI BLAST analysis (Altschul et al., 1997, Nucleic Acids Res. 25(17):3389-402.) of the amplification primer and dual-labeled probe nucleotide sequences against the GenBank "nr" nucleotide database revealed HSV-1 and HSV-2 as the only identical matches. As the GenBank database is incomplete and the specificity of the amplification procedure is of the highest priority for clinical diagnostics, DNA was extracted from 37 human pathogens of viral, bacterial, and fungal origin (Table II) purchased from American Type Cultures Collection (ATCC). DNA from each was tested for cross-reactivity and none was detectable. Whereas both the HSV-1/2 Rev+For and HSV2a-1+2 primer combinations will amplify HSV-1 and HSV-2, the dual-labeled probes were designed to discriminate between the two viruses. The HSV-1 probe was designed such that only 12 of 31 nucleotides (38.7%) were complementary to the HSV-2 genome while the HSV-2 probe has only 12 of 27 nucleotides (44.4%) complementary to HSV-1. As a result in all analyses, the HSV-1 template DNA was not detectable by the HSV-2 probe in the 625 nm/660 hp acquisition channel and HSV-2 DNA was not detectable with the HSV-1 probe in the 470 nm/510 nm acquisition channel.

TABLE II

Bacterial, viral, and fungal pathogens for which the specificity of the HSV primers and probes were assessed.

Bacteria:

*Anaplasma phagocytophilum* (VR-1455)[1]
*Babesia microti* (30222)
*Bacteroides fragilis* (23745)
*Bartonella bacilliformis* (35685)
*Bartonella henselae* (49882)
*Bartonella quintana* (51694)
*Borrelia burgdorferi* (35210)
*Brucella ovis* (25840)
*Chlamydia pneumoniae* (VR-1356)
*Chlamydia trachomatis* (VR-901B)
*Gardnerella vaginalis* (14018)
*Helicobacter pylori* (43579)
*Mobiluncus curtisii* (35241)
*Mobiluncus mulieris* (35243)
*Mycoplasma fermentans* (15474)
*Mycoplasma genitalium* (49857)
*Mycoplasma hominis* (14027)
*Mycoplasma pneumoniae* (15377)
*Neisseria gonorrhoeae* (27628)
*Trichomonas vaginalis* (30246)
*Ureaplasma urealyticum* (27618)

Viruses:

Adenovirus (VR-1)
Cytomegalovirus (CMV; VR-807)
Coxsackie Virus (VR-184)
Epstein-Barr Virus (EBV; CCL-86)
HHV-6 (VR-1467)
HHV-8 (CRL-2230)
HPV-16 (CRL-1550)
HTLV-I (CRL-8294)
Varicella-zoster virus (VZV, VR-795)

Fungi:

*Aspergillus fumigatus* (14110)
*Candida albicans* (11651)
*Candida glabrata* (32312)
*Candida parapsilosis* (10265)
*Candida tropicalis* (10610)
*Cryptococcus neoformans* (2344)
*Trichosporan cutaneum* (4151)

[1]The ATCC catalogue designation is listed in parentheses after each organism.

Interference Analysis

To verify that components of a cervicovaginal swab DNA extraction do not inhibit or decrease the efficiency of the real-time PCR reaction, 0.5 µg of two HSV-negative DNA extracts were separately incubated in the presence of decreasing concentrations of the plasmid positive control from $10^9$ through 10 copies/reaction. In this range, no significant difference in $C_T$ score was apparent between the presence or absence of DNA extracted from cervicovaginal swab specimens.

Pyrosequencing Analysis

A Pyrosequencing procedure was adopted for two independent PCR reactions which utilized forward and reverse orientation primers capable of amplifying both HSV-1 and HSV-2 DNA. The nucleotide sequence of the regions between these primers were identified by Pyrosequencing to classify each amplicon as either HSV-1 or HSV-2. By using the Pyrosequencing data as a standard, sensitivity and specificity scores of 100.0% were calculated for both the HSV-1 and HSV-2 probes (Table III).

TABLE III

Specificity and sensitivity calculations for the real-time HSV-1 and HSV-2 probe reactions.

(A) HSV-1

| HSV-1 Real-time PCR Result | No. of samples with the following Pyrosequencing result: | | |
|---|---|---|---|
| | Positive (HSV-1) | Negative | Total |
| Positive | 19 | 0 | 19 |
| Negative | 0 | 100 | 100 |
| Total | 19 | 100 | 119 |

(B) HSV-2

| HSV-2 Real-time PCR Result | No. of samples with the following Pyrosequencing result: | | |
|---|---|---|---|
| | Positive (HSV-2) | Negative | Total |
| Positive | 42 | 0 | 42 |
| Negative | 0 | 78 | 78 |
| Total | 42 | 78 | 120 |

(C) Summary of Results

| | Sensitivity | Specificity | Agreement |
|---|---|---|---|
| HSV-1 | 100% (19/19) | 100% (100/100) | 100% (119/119) |
| HSV-2 | 100% (42/42) | 100% (78/78) | 100% (120/120) |

Two sets of amplification primers (Table I) were selected for Pyrosequencing analysis to reduce the possibility of false negative results, which could be inherent to utilizing one non-characterized primer pair for molecular amplification.

Clinical Application of the HSV-1/HSV-2 Real-Time PCR Assay

TABLE IV

Population statistics and HSV positivity rate for cervicovaginal specimens tested.

| State | Population | HSV-1 or HSV-2 | HSV-1 | HSV-2 |
|---|---|---|---|---|
| Texas | 1965 (42.3%)[a] | 211 (10.7%)[b] | 61 (3.1%)[b] | 150 (7.6%)[b] |
| New Jersey | 956 (20.9%) | 90 (9.4%) | 33 (3.5%) | 56 (5.9%) |
| Florida | 803 (17.5%) | 96 (12.0%) | 21 (2.6%) | 75 (9.3%) |
| Pennsylvania | 171 (3.7%) | 17 (9.9%) | 4 (2.3%) | 13 (7.6%) |

TABLE IV-continued

Population statistics and HSV positivity rate for cervicovaginal specimens tested.

|  | Population | HSV-1 or HSV-2 | HSV-1 | HSV-2 |
|---|---|---|---|---|
| Georgia | 149 (3.2%) | 24 (16.1%) | 2 (1.3%) | 22 (14.8%) |
| Other | 184 (4.0%) | 24 (13.0%) | 7 (3.8%) | 17 (9.2%) |
| Total | 4581 | 479 (10.5%) | 133 (2.9%) | 345 (7.5%) |
| Age |  |  |  |  |
| 0-10 | 30 | 1 (3.3%) | 1 (3.3%) | 0 (0.0%) |
| 11-20 | 674 | 74 (11.0%) | 34 (5.0%) | 40 (5.9%) |
| 21-30 | 1615 | 162 (10.0%) | 51 (3.2%) | 111 (6.9%) |
| 31-40 | 1099 | 109 (9.9%) | 23 (2.1%) | 86 (7.8%) |
| 41-50 | 639 | 67 (10.5%) | 14 (2.2%) | 53 (8.3%) |
| 51-60 | 319 | 43 (13.5%) | 7 (2.2%) | 36 (11.3%) |
| 61-70 | 126 | 15 (11.9%) | 1 (0.8%) | 14 (11.1%) |
| 71-80 | 60 | 4 (6.7%) | 1 (1.7%) | 3 (5.0%) |
| 81-90 | 17 | 3 (17.6%) | 2 (11.8%) | 1 (5.9%) |
| 91-100 | 2 | 1 (50.0%) | 0 (0.0%) | 1 (50.0%) |

$^a$= Percent of the total population.
$^b$= Percent positive in this category (state or age).

From the analysis of the positive HSV specimens in our laboratory, 133/479 (27.8%, 95% CI, 24.0-32.0%) and 346/479 (72.2%, 95% CI, 68.0-76.2%) were infected with HSV-1 and HSV-2, respectively. The mean age of those infected with HSV-1 was 29.5±13.5 compared with 35.6±13.9 for HSV-2 infections. A chi-square analysis did not identify a significant difference between the HSV-1 and HSV-2 positively rate of those states in which over 130 specimens were collected and analyzed (p=0.112).

The present invention includes, but is not limited to, PCR methods as well as primers and probes for detecting and specifically identifying and discriminating the presence of HSV-1 and HSV-2 in a sample in a single tube reaction, for example.

Examples of this type are disclosed herein wherein the first amplicon and the second amplicon contain at least a segment of the open reading frame of the gene encoding glycoprotein B. The forward primer may comprise, for example, the nucleotide sequence: 5'-ttctgcagctcgcaccac-3' (SEQ ID NO:5). An example forward primer consists of SEQ ID NO:5. The reverse primer may comprise, for example, the nucleotide sequence: 5'-ggagcgcatcaagaccacc-3' (SEQ ID NO:6). An example reverse primer consists of SEQ ID NO:6.

Exemplary methods disclosed herein are wherein the first probe is a nucleic acid molecule capable of hybridizing to one of the strands of the first amplicon, and wherein the second probe is a nucleic acid molecule capable of hybridizing to one of the strands of the second amplicon. With regard to HSV-1 and HSV-2, for example, the first probe may comprise, for example, the nucleotide sequence: 5'-cgatggcaacgcggcccaa-catatcgttgac-3' (SEQ ID NO:7). An example first probe consists of SEQ ID NO:7. The second probe may comprise, for example, the nucleotide sequence: 5'-cgatgcgcccagcatgtcgt-tcacgt-3' (SEQ ID NO:8). An example second probe consists of SEQ ID NO:8.

Methods of the present invention further comprise, for example, determining the nucleotide sequence of at least a segment of (1) the first amplicon if the first amplicon is produced in (b), and (2) the second amplicon if the second amplicon is produced in (b).

An example method for ascertaining whether a sample includes a first strain of a herpesvirus or a second strain of a herpesvirus, comprises (a) providing (1) a nucleic acid from the sample, (2) a forward primer, and (3) a reverse primer, wherein a combination comprising the forward primer and the reverse primer is capable of amplifying, by the polymerase chain reaction, a segment of the genome of (1) the first strain to produce a first amplicon, and (2) the second strain to produce a second amplicon, and wherein the nucleotide sequence of the first amplicon and the nucleotide sequence of the second amplicon are not identical, (b) incubating a combination comprising the nucleic acid from the sample, the forward primer, and the reverse primer under conditions allowing production of (1) the first amplicon if the sample contains the first strain, and (2) the second amplicon if the sample contains the second strain, and (c) ascertaining that (1) the sample does not contain the first strain or the second strain if the first amplicon and the second amplicon are not produced in (b), (2) the sample contains the first strain and does not contain the second strain if the first amplicon is produced in (b) and the second amplicon is not produced in (b), (3) the sample does not contain the first strain and does contain the second strain if the first amplicon is not produced in (b) and the second amplicon is produced in (b), or (4) the sample contains the first strain and the second strain if the first amplicon and the second amplicon are produced in (b).

In exemplary methods disclosed herein, (a) further comprises providing a first probe specific to the first strain, and (c) further comprises determining that the first amplicon is produced in (b) if a first signal generated from the first probe is detected.

Furthermore, in exemplary methods disclosed herein, (a) further comprises providing a second probe specific to the second strain, and wherein (c) further comprises determining that the second amplicon is produced in (b) if a second signal generated from the second probe is detected.

Moreover, in exemplary methods disclosed herein, (a) further comprises providing (1) a first probe specific to the first strain, and (2) a second probe specific to the second strain, and wherein (c) further comprises determining that (1) the first amplicon is produced in (b) if a first signal generated from the first probe is detected, and (2) the second amplicon is produced in (b) if a second signal generated from the second probe is detected.

Additionally, in exemplary methods disclosed herein, the combination of (b) further comprises the first probe and the second probe, and wherein a single vessel contains the combination of (b).

Methods of the present invention are particularly described wherein the first strain of the herpesvirus is HSV-1, and wherein the second strain of the herpesvirus is HSV-2. Methods are exemplified wherein the first amplicon and the second amplicon contain at least a segment of the open reading frame of the gene encoding glycoprotein B; wherein the forward primer comprises the nucleotide sequence: 5'-ttctgcagctcg-caccac-3' (SEQ ID NO:5); wherein the forward primer consists of SEQ ID NO:5; wherein the reverse primer comprises the nucleotide sequence: 5'-ggagcgcatcaagaccacc-3' (SEQ ID NO:6); wherein the reverse primer consists of SEQ ID NO:6.

Methods are preferred wherein the first probe is a nucleic acid molecule capable of hybridizing to one of the strands of the first amplicon and wherein the second probe is a nucleic acid molecule capable of hybridizing to one of the strands of the second amplicon.

Methods of the present invention may be employed wherein the first probe comprises the nucleotide sequence 5'-cgatggcaacgcggcccaacatatcgttgac-3' (SEQ ID NO:7), for example, wherein the first probe consists of SEQ ID NO:7.

Methods of the present invention may be employed wherein the second probe comprises the nucleotide sequence: 5'-cgatgcgccccagcatgtcgttcacgt-3' (SEQ ID NO:8), for example, wherein the second probe consists of the sequence: 5'-cgatggcaacgcggcccaacatatcgttgac-3' (SEQ ID NO:7). The second probe may, for example, consists of the nucleotide sequence: 5'-cgatgcgccccagcatgtcgttcacgt-3' (SEQ ID NO:8).

Methods of the present invention encompass, for example, wherein (c), supra, further comprises determining the nucleotide sequence, e.g., by means of Pyrosequencing, at least a segment of (1) the first amplicon if the first amplicon is produced in (b), and (2) the second amplicon if the second amplicon is produced in (b).

Related Methods and Compositions

Subject matter of the present invention disclosed herein, for example, is an isolated composition for the detection and distinct identification of HSV-1 and HSV-2 comprising a first oligonucleotide primer, at least 8 nucleotides in length, common to a region within positions 978 to 1149 (5-3') of SEQ ID NO:2 and the corresponding homolog region of SEQ ID NO:1, and a second oligonucleotide primer, at least 8 nucleotides in length, that is common to a region within positions 1348 to 1546 (5-3') of SEQ ID NO:3 and the corresponding homolog region of SEQ ID NO:4. Compositions are preferred wherein at least one of the oligonucleotide primers is at least 10 nucleotides in length. Compositions of the present invention are preferred wherein one of the oligonucleotide primers is at least 10 nucleotides in length and one of the oligonucleotide primers is at least 12 nucleotides in length. Compositions of the present invention are preferred wherein each of the oligonucleotide primers is at least 12 nucleotides in length. An exemplary composition of the present invention is wherein the first oligonucleotide primer is common to a region within positions 1002 to 1149 (5-3') of SEQ ID NO:2 and the corresponding homolog region of SEQ ID NO:1. Each oligonucleotide primer which comprises a species of sequence specified in a Markush group herein, e.g., examples specified in each 'Markush group' infra, is contemplated independently. Preferred examples, for example, are wherein the first oligonucleotide primer comprises a sequence selected from the group consisting of (5-3') positions 1002-1010, 1003-1011, 1004-1012, 1005-1013, 1006-1014, 1007-1015, 1008-1016, 1009-1017, 1010-1018, 1011-1019, 1012-1020; 1013-1021, 1014-1022, 1015-1023, and 1016-1024 of SEQ II) NO:2 (each sequence is independently contemplated as is each species sequence recited herein). Preferred alternate examples are wherein the first oligonucleotide primer comprises a sequence selected from the group consisting of (5-3') positions 1041-1049, 1042-1050, 1043-1051, 1044-1052, 1045-1053, 1046-1054, 1047-1055, 1048-1056, 1049-1057, 1050-1058, 1051-1059, and 1052-1060 of SEQ ID NO:2. Further preferred alternate examples are wherein the first oligonucleotide primer comprises a sequence selected from the group consisting of (5-3') positions 1071-1079, 1072-1080, 1073-1081, 1074-1082, 1075-1083, 1076-1084, 1077-1085, 1078-1086, 1079-1087, 1080-1088, 1081-1089, and 1082-1090 of SEQ ID NO:2. Preferred examples are wherein the first oligonucleotide primer comprises a sequence selected from the group consisting of (5-3') positions 1092-1100, 1093-1101, 1094-1102, 1095-1103, 1096-1104, 1097-1105, 1098-1106, 1099-1107, 1100-1108, 1101-1109, 1102-1110, and 1103-1111 of SEQ ID NO:2. Preferred alternate examples are wherein the first oligonucleotide primer comprises a sequence selected from the group consisting of (5-3') positions 1113-1121, 1114-1122, 1115-1123, 1116-1124, 1117-1125, 1118-1126, and 1119-1127 of SEQ ID NO:2.

An exemplary composition of the present invention is wherein the first oligonucleotide primer is common to a region within positions 1002 to 1149 (5-3') of SEQ ID NO:2 and the corresponding homolog region of SEQ ID NO:1.

Compositions described herein are preferred wherein the first oligonucleotide primer is common to a region within positions 1002 to 1149 (5-3') of SEQ ID NO:2 and the corresponding homolog region of SEQ ID NO:1, for example, wherein the first oligonucleotide primer is common to a region within positions 1128 to 1149 (5-3') of SEQ ID NO:2. Isolated composition for the detection and distinct identification of HSV-1 and HSV-2 are preferred wherein the first oligonucleotide primer comprises a sequence selected from the group consisting of (5-3') positions 1128-1136, 1129-1137, 1130-1138, 1131-1139, 1132-1140, 1133-1141, 1134-1142, 1135-1143, 1136-1144, 1137-1145, 1138-1146, 1139-1147, 1140-1148, and 1141-1149 of SEQ ID NO:2.

Subject matter of the present invention disclosed herein, for example, is an isolated composition for the detection and distinct identification of HSV-1 and HSV-2 comprising: a first oligonucleotide primer, at least 8 nucleotides in length, common to a region within positions 978 to 1149 (5-3') of SEQ ID NO:2 and the corresponding homolog region of SEQ ID NO:1, and a second oligonucleotide primer, at least 8 nucleotides in length, that is common to a region within positions 1348 to 1546 (5-3') of SEQ ID NO:3 and the corresponding homolog region of SEQ ID NO:4. Compositions are preferred wherein the second oligonucleotide primer is common to a region within positions 1457 to 1546 (5-3') of SEQ ID NO:4 and the corresponding homolog region of SEQ ID NO:3.

Preferred examples are wherein the second oligonucleotide primer comprises a sequence selected from the group consisting of (5-3') positions 1538 to 1546, 1537 to 1545, 1536 to 1544, 1535 to 1543, 1534 to 1542, and 1533 to 1541 of SEQ ID NO:4. Alternate preferred examples are wherein the second oligonucleotide primer comprises a sequence selected from the group consisting of (5-3') positions 1521-1529, 1520-1528, 1519-1527, 1518-1526, 1517-1525, 1516-1524, and 1515-1523 of SEQ ID NO:4. Alternate preferred examples are wherein the second oligonucleotide primer comprises a sequence selected from the group consisting of (5-3') positions 1504-1512, 1503-1511, 1502-1510, and 1501-1509 of SEQ ID NO:4. Alternate preferred examples are wherein the second oligonucleotide primer comprises a sequence selected from the group consisting of (5-3') positions 1491-1499, 1490-1498, 1489-1497, 1488-1496, 1487-1495, 1486-1494, 1485-1493, 1484-1492, 1483-1491, 1482-1490, 1481-1489, 1480-1488, 1479-1487, 1478-1486, 1477-1485, 1476-1484, 1475-1483, 1474-1482, 1473-1481, 1472-1480, 1471-1479, 1470-1478, 1469-1477, 1468-1476, 1467-

1475, 1466-1474, 1465-1473, 1464-1472, 1463-1471, 1462-1470, 1461-1469, 1460-1468, 1459-1467, and 1458-1466 of SEQ ID NO:4.

Further compositions of the present invention for the detection and distinct identification of HSV-1 and HSV-2 which comprise a first oligonucleotide primer, at least 8 nucleotides in length, common to a region within positions 978 to 1149 (5-3') of SEQ ID NO:2 and the corresponding homolog region of SEQ ID NO:1, and a second oligonucleotide primer, at least 8 nucleotides in length, that is common to a region within positions 1348 to 1546 (5-3') of SEQ ID NO:3 and the corresponding homolog region of SEQ ID NO:4, further comprise a first oligonucleotide probe between about 15 and about 40 nucleotides in length specific to a sequence selected from the group consisting of SEQ ID NO:1 and SEQ ID NO:3 and a second oligonucleotide probe between about 15 and about 40 nucleotides in length specific to a sequence selected from the group consisting of SEQ ID NO:2 and SEQ ID NO:4. Compositions are preferred wherein the first probe is specific to a nucleotide sequence within positions 978 to 1384 SEQ ID NO:2 or an exact complement thereof, and the second oligonucleotide probe is specific to the corresponding homolog region of SEQ ID NO:1 or an exact complement thereof. Compositions of this type are preferred wherein the first probe is specific to a nucleotide sequence within positions 1002 to 1269 SEQ ID NO:2 or an exact complement thereof, and the second oligonucleotide probe is specific to the corresponding homolog region of SEQ ID NO:1 or an exact complement thereof. Compositions of this type are further preferred wherein the first probe is specific to a nucleotide sequence within positions 1126 to 1230 SEQ ID NO:2 or an exact complement thereof, and the second oligonucleotide probe is specific to the corresponding homolog region of SEQ ID NO:1 or an exact complement thereof. Compositions of this type are further preferred wherein the first probe is specific to a nucleotide sequence within positions 1140 to 1190 SEQ ID NO:2 or an exact complement thereof, and the second oligonucleotide probe is specific to the corresponding homolog region of SEQ ID NO:1 or an exact complement thereof.

Compositions according to the present invention are preferred wherein the first and second oligonucleotide probes are each detectably labeled with distinctly different detectable labels.

The present invention is directed toward a real-time method for detecting and identifying distinct species of nucleic acids, in a single container, from a certain genus of infectious agents comprising providing a forward PCR primer common to a homologous gene region between the distinct species, and providing a reverse PCR primer common to a homologous gene region between the distinct species, to thereby define a PCR target region amongst the species, and providing a first oligonucleotide probe specific to a nucleic acid sequence within the target region that is characteristic of a first species, providing a second oligonucleotide probe specific to a nucleic acid sequence within the target region that is characteristic of a second species, wherein the first and second oligonucleotide probes are each detectably labeled with distinctly different detectable labels, conducting a PCR reaction in the container by means of the primers to amplify the target region amongst the species, and detecting the distinct labels, thereby identifying distinct species of nucleic acids corresponding to distinct species of infectious agents. These methods of the present invention are preferred wherein the infectious agent is a member of the Herpesviridae family. Methods are preferred wherein the first oligonucleotide probe is between about 15 and about 40 nucleotides in length specific to a sequence selected from the group consisting of SEQ ID NO:1 and SEQ ID NO:3 and a second oligonucleotide probe between about 15 and about 40 nucleotides in length specific to a sequence selected from the group consisting of SEQ ID NO:2 and SEQ ID NO:4. Methods are particularly preferred wherein the genus of infectious agents is HSV-1 and HSV-2 and the forward PCR primer is common to a region within positions 978 to 1149 (5-3') of SEQ ID NO:2 and the corresponding homolog region of SEQ ID NO:1, and the reverse PCR primer is common to a region within positions 1348 to 1546 (5-3') of SEQ ID NO:4 and the corresponding homolog region of SEQ ID NO:3. A method of this type is preferred wherein the first probe is specific to a nucleotide sequence within positions 978 to 1384 SEQ ID NO:2 or an exact complement thereof, and the second oligonucleotide probe is specific to the corresponding homolog region of SEQ ID NO:1 or an exact complement thereof.

EXAMPLES

Example I

HSV-1 and HSV-2 controls and Clinical Specimens

Confirmed HSV-1 (#VR-539) and HSV-2 (#VR-734) specimens originally isolated from a human encephalitis brain specimen and a genital infection, respectively, were purchased from the American Type Cultures Collection (ATCC, Manassas, Va.). Clinical specimens were submitted to our laboratory for HSV testing from November 2003 through January 2004 by obstetrician/gynecologist offices. Information describing the clinical presentation of the patients was not provided. Cervicovaginal sampling was performed with a Cellmatics swab (BD, Sparks, Md.) that was placed in 2 ml viral transport medium. Upon receipt to the laboratory, DNA was extracted by mixing 470 µl of the transport media with 25 µl of 10% sodium dodecyl sulfate and 12 µl of freshly prepared DNase-free 10 mg/ml proteinase-K, and incubating for 2 hours at 55° C. DNA was phenol:chloroform:isoamyl alcohol extracted and recovered by ethanol precipitation. DNA was pelleted, dried in a speed vacuum, and resuspended in 20 µl TE buffer. Absorbance was monitored by 260/280 readings with a BioPhotometer spectrophotometer (Eppendorf, Westbury, N.Y.) and the DNA concentration was adjusted to 0.2 µg/µl prior to PCR analysis.

Example II

Conventional PCR Amplification Parameters

Each 50 µl reaction contained 1 µg template DNA, 1×PCR buffer, 1.5 mM MgCl$_2$, 0.25 mM dNTP (dATP, dCTP, dGTP, and dTTP), 0.2 µM HSV2a-1, 0.2 µM HSV2a-2, and 2.5 U Taq DNA polymerase (USB, Cleveland, Ohio). Cycling conditions included an initial denaturation step of 94° C. for 3 minutes followed by 30 cycles of 94° C. for 1 min, 53° C. for 1 min, and 72° C. for 1 min in a T3 Thermocycler (Biometra, Göttingen, Germany). A 10 min extension step at 72° C. concluded each reaction. PCR products were resolved through a 2% agarose gel containing 0.5 µg/ml ethidium bromide and visualized with a SynGene Gel Documentation System (Frederick, Md.). The amplification target of the reaction was the HSV glycoprotein B gene and resulted in a 342 bp fragment; both HSV-1 and HSV-2 are amplified with this primer pair combination (Cone et al., 1991, J. Infect. Dis. 164(4):757-60.).

Example III

Preparation of HSV-1 and HSV-2 Vector Controls

Positive controls for each probe were generated by subcloning amplicons derived from using forward and reverse orientation amplification primers and template DNA extracted from HSV-1 and HSV-2 ATCC-purchased controls. Amplicons were subcloned into the pCRII-TOPO vector of the TOPO TA Cloning Dual Promoter kit (Invitrogen, Carlsbad, Calif.) according to the manufacturer's instructions. The correct constructs were identified by colony PCR and restriction digestion by standard molecular biology procedures (Ausubel et al., 1997, Nucleic Acids Res. 25(17):3389-402.). Large-scale plasmid preparations for each were prepared with the Qiagen plasmid extraction kit and quantitated.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

What is claimed is:

1. A single vessel assay system with a sensitivity of 100% and a specificity of 100% for the simultaneous detection and distinct identification of HSV-1 and HSV-2, comprising:
   (a) a single vessel;
   (b) a single set of forward and reverse primers present in said single vessel targeting against glycoprotein B gene of herpes virus, said forward primer consists of SEQ ID NO: 5 and said reverse primer consists of SEQ ID NO: 6;
   (c) a first probe present in said single vessel, said first probe consists of SEQ ID NO: 7 and selectively hybridizes to a HSV-1 amplicon produced by said single set of forward and reverse primers in a real-time polymerase chain reaction when HSV-1 is present; and
   (d) a second probe present in said single vessel, said second probe consists of SEQ ID NO: 8 and selectively hybridizes to a HSV-2 amplicon produced by said single set of forward and reverse primers in said real-time polymerase chain reaction when HSV-2 is present, said first probe and said second probe each has a different detectable label, said hybridization of said first probe to said HSV-1 amplicon and said second probe to said HSV-2 amplicon provides the simultaneous detection and distinct identification of HSV-1 and HSV-2 in a single tube reaction having a sensitivity of 100% and a specificity of 100%.

2. The single vessel assay system of claim 1, further comprising: (e) a pyrosequencing reagent, said pyrosequencing reagent is used for determining the nucleotide sequence of said HSV-1 amplicon and said HSV-2 amplicon.

* * * * *

```
                        SEQUENCE LISTING

<160> NUMBER OF SEQ ID NOS: 12

<210> SEQ ID NO 1
<211> LENGTH: 2716
<212> TYPE: DNA
<213> ORGANISM: herpes simplex virus type 1

<400> SEQUENCE: 1
atcacaggtc gtcctcgtcg gcgtcaccgt ctttgttggg aacttgggtg tagttggtgt      60
tgcggcgctt gcgcatgacc atgtcggtga ccttggcgct gagcagcgcg ctcgtgccct     120
tcttcttggc cttgtgttcc gtgcgctcca tggcagacac cagggccatg taccgtatca     180
tctcccgggc ctcggctagc ttggcctcgt caaagtcgcc gccctcctcg ccctccccgg     240
acgcgtccgg gttggtgggg ttcttgagct ccttggtggt tagcgggtac agggccttca     300
tggggttgct ctgcagccgc atgacgtagc gaaaggcgaa gaaggccgcc gccaggccgg     360
ccaggaccaa cagacccacg gccagcgccc caaagggtt ggacatgaag gaggacacgc      420
ccgacacggc cgataccacg ccgcccacga tgcccatcac caccttgccg accgcgcgcc     480
ccaggtcgcc catcccctcg aagaacgcgc ccaggcccgc aaacatggcg gcgttggcgt     540
cggcgtggat gaccgtgtcg atgtcggcga agcgcaggtc gtgcagctgg ttgcggcgct     600
ggacctccgt gtagtccagc aggccgctgt ccttgatctc gtggcgggtg tacacctcca     660
gggggacaaa ctcgtgatcc tccagcatgg tgatgttgag gtcgatgaag gtgctgacgg     720
tggtgatgtc ggcgcggctc agctggtggg agtacgcgta ctcctcgaag tacacgtagc     780
ccccaccgaa ggtgaagtag cgccggtgtc ccacggtgca cggctcgatc gcatcgcgcg     840
tcagccgcag ctcgttgttc tcccccagct gcccctcgac caacgggccc tggtcttcgt     900
accgaaagct gaccaggggg cggctgtagc aggcccgggg ccgcgagctg atgcgcatcg     960
agttttggac gatcacgttg tccgcggcga ccggcacgca cgtggagacg gccatcacgt    1020
cgccgagcat ccgcgcgctc acccgccggc ccacggtggc cgaggcgatg gcgttggggt    1080
tcagcttgcg ggcctcgttc cacagggtca gctcgtgatt ctgcagctcg caccacgcga    1140
tggcaacgcg gcccaacata tcgttgacat ggcgctgtat gtggttgtac gtaaactgca    1200
gcctggcgaa ctcgatggag gaggtggtct tgatgcgctc cacggacgcg ttggcgctgg    1260
ccccgggcgg cggggcgtg gggtttgggg gcttgcggct ctgctcgcgg aggtgttccc     1320
gcacgtacag ctccgcgagc gtgttgctga aaggggctg gtacgcgatc agaaagcccc     1380
cattggccag gtagtactgc ggctggccca ccttgatgtg cgtcgcgttg tacctgcggg    1440
cgaagatgcg gtccatggcg tcgcgggcgt ccttgccgat gcagtccccc aggtccacgc    1500
gcgagagcgg gtactcggtc aggttggtgg tgaaggtggt ggatatggcg tcggaagaga    1560
```

```
atcggaagga gccgccgtac tcggagcgca gcatctcgtc cacctcctgc cacttggtca    1620
tggtgcagac cgacgggcgc tttggcaccc agtcccaggc cacggtgaac ttggggtcg    1680 tgagcaggtt ccgggtggtc ggcgccgtgg cccgggcctt ggtggtgagg tcgcgcgcgt    1740
agaagccgtc gacctgcttg aagcggtcgg cggcgtagct ggtgtgttcg gtgtgcgacc    1800
cctcccggta gccgtaaaac ggggacatgt acacaaagtc gccagtcgcc aacacaaact    1860
cgtcgtacgg gtacaccgag cgcgcgtcca cctcctcgac gatgcagttt accgtcgtcc    1920
cgtaccggtg gaacgcctcc acccgcgagg ggttgtactt gaggtcggtg gtgtgccagc    1980
cccggctcgt gcgggtcgcg gcgttggccg gtttcagctc catgtcggtc tcgtggtcgt    2040
cccggtgaaa cgcggtggtc tccaggttgt tgcgcacgta cttggccgtg gaccgacaga    2100 ccccccttggc gttgatcttg tcgatcacct cctcgaaggg gacggggggcg cggtcctcaa    2160 agatccccat aaaactggga tagcggtggc cgaaccacac ctgcgaaacg gtgacgtctt    2220
tgtagtacat ggtggccttg aacttgtacg gggcgatgtt ctccttgaag accaccgcga    2280
tgccctccgt gtagttctga ccctcgggcc gggtcgggca gcggcgcggc tgctcgaact    2340
gcaccaccgt ggcgcccgtg gggggtgggc acacgtaaaa gtttgcatcg gtgttctccg    2400
ccttgatgtc ccgcaggtgc tcgcgcaggg tggcgtggcc cgcggcgacg gtcgcgttgt    2460
cgccggcggg gcgcggcggc tttgggggtt tcggttttct gttcttcttc ggtttcgggt    2520
cccccgttgg ggggcgcca ggggcgggcg gcgccggagt ggcagggccc ccgttcgccg    2580
cctgggtcgc ggccgcgacc ccaggcgtgc cggggggaact cggagccgcc gacgccacca    2640 ggaccccccag cgtcaacccc aagagcgccc atacgacgaa ccaccggcgc ccccgcgcgg    2700
gggcgccctg gcgcat                                                    2716

<210> SEQ ID NO 2
<211> LENGTH: 2716
<212> TYPE: DNA
<213> ORGANISM: herpes simplex virus type 2

<400> SEQUENCE: 2
cttagagctc gtcttcgtct ccggcctcgt cctcgttgtg gagcggagag tacctggctt      60
tgttgcgctt gcgcagaacc atgttggtga ccttggagct gagcagggcg ctcgtgccct     120
tctttctggc cttgtgttcc gtgcgctcca tggccgacac caaagccata tatcggatca     180
tttctcgggc ctcggccaac ttggcctcgt caaacccgcc ccctccgcg ccttcctccc      240 cctcccgcc cacgccccg gggtcggaag tcttgagttc cttggtggtg agcggataca       300
gggccttcat gggattgcgt tgcagttgca ggacgtagcg gaaggcgaag aaggccgcga    360
ccaggccggc caggaccagc agccccacgg caagcgcccc gaaggggttg gacataaagg      420
aggacacgcc cgagacggcc gacaccacgc ccccactac tcccatgact accttgccga      480
ccgcgcgccc caagtccccc atccctcga agaacgcgca cagccccgcg aacatggcgg      540
cgttggcgtc ggcgcggatg accgtgtcga tgtcggcaaa gcgcaggtcg tgcagctggt      600
tgcggcgctg gacctccgtg tagtccagca ggccgctgtc cttgatctcg tggcgcgtgt      660
agacctccag gggcacaaac tcgtggtcct ccagcatggt gatgttcagg tcgatgaagg      720
tgctgacggt ggtgacgtcg gcgcgactca gctggtgaga gtacgcgtac tcctcgaagt     780
acacgtagcc cccgccgaag atgaagtagc gccggtggcc cacggtgcac ggctcgagcg      840
cgtcgcgggt gaggcgcagc tcgttgttct cgcccagctg cccctcgatc agcgggccct      900
ggtcttcgta ccgaaagctg accaggggc ggctgtagca cgtcccggc cgcgagctga       960
```

```
cgcgcatcga gttctgcacg atcacgttgt ccggggcgac gggcacgcac gtggagacgg   1020
ccatgacgtc tccgagcatg cgcgcgctca cccgccggcc gacggtggcg gaggcgatgg   1080
cgttggggtt gagcttgcgg gcctcgttcc agagagtcag ctcgtggttc tgcagctcgc   1140
accacgcgac ggcgatgcgc cccagcatgt cattcacgtg gcgctgtatg tggttatacg   1200
taaactgcag ccgggcgaac tcgatcgagg aggtggtctt gatgcgctcc acggacgcgt   1260
tggcgctggg cgcctcccgc agtggcgcgg gcgtggcatt ccggggcttg cggtcctgct   1320
cccgcatgta ctcccgcacg tacagctcgg cgagcgtgtt gctgaggagg ggctggtacg   1380
cgatgaggaa ccccccgtg gccaggtagt actgcggctg gcccaccttg atgtgcgtgg    1440
cgttgtactt gcgcgcaaac atgcggtcga tggcctcgcg ggcatcccgg ccgatgcagt   1500
cgcccaggtc gacgcgcgag agcgagtact cggtcaggtt ggtggtgaag gtggtcgaga   1560
tggcgtcgga ggagaagcgg aaggagccgc cgtactcggc gcggagcatc tcgtccacct   1620
cctgccactt ggtcatggtg cagaccgccg gtcgcttcgg cacccagtcc caggccacgg   1680
taaacttggg ggtcgtcagc aagttgcggg tcgtcggcga cgtggcccgg gccttcgtgg   1740
tgaggtcgcg cgcgtagaag ccgtcgacct gcttgaagcg gtcggcggcg tagctggtgt   1800
gctcggtgtg cgacccctcc cggtagccgt aaaacgggga catgtacaca agtcgcccg    1860 tcgccagcac aaactcatcg tacgggtaca ccgaccgcgc gtccacctcc tcgacgatgc   1920
agttgaccgt cgtgccgtac cgatggaacg cctccacccg cgaggggttg tacttgaggt   1980
cggtggtgtg ccaccccgg ctcgtgcgcg tggcgacctt cgccggcttg agctccatgt    2040
cggtctcgtg gtcgtcccgg tgaaacgcgg tggtctccat gttgttccgc acgtacttgg   2100
ccgtggagcg gcagacccc ttggtgttaa tcttgtcgat cacctcctcg aagggaacgg    2160
gggcgcggtc ctcgaatatc cccataaact gggagtagcg gtggccgaac cacacctgcg   2220
acacggtcac gtctttgtag tacatggtgg ccttgaattt gtacggggcg atgttctcct   2280
tgaagaccac cgcgatgccc tccgtgtagt tctgccctc cggcgcgtc gggcagcggc     2340 gcggctgctc aaactgcacc accgtggcgc ccgtcggggg cggcacacg taaaactggg    2400 catcggcgtt ctcgaccttg atttcccgca ggtgcgcgcg cagcgtggcg tggcggcgg    2460 cgacggtcgc gttggcgtcg gggggcgggg tcgcctcggg ccgcttgggc ggcttttttgg  2520 ttttccgctt ccgggccttg gtggtcgcgg ggctcgggac gggggggcggc cgggaggcgg  2580 gaccccgtt cgccgcgacg gtcgcggcca cgccgcccga ggcgcggggg gccgccgggg    2640
ccgccggggc cgccgacgcc accgcggcca ccagcgcccc cacgaccagc gcgcaaatca   2700
agcccccccc gcgcat                                                   2716

<210> SEQ ID NO 3
<211> LENGTH: 2716
<212> TYPE: DNA
<213> ORGANISM: herpes simplex virus type 1

<400> SEQUENCE: 3
atgcgccagg gcgcccccgc gcggggggcgc cggtggttcg tcgtatgggc gctcttgggg     60
ttgacgctgg gggtcctggt ggcgtcgcg gctccgagtt cccccggcac gcctgggtc      120 gcggccgcga cccaggcggc gaacgggggc cctgccactc cggcgccgcc cgcccctggc    180
gcccccccaa cggggggaccc gaaaccgaag aagaacagaa aaccgaaacc cccaaagccg   240
ccgcgccccg ccgccgacaa cgcgaccgtc gccgcgggcc acgccaccct gcgcgagcac   300
ctgcgggaca tcaaggcgga gaacaccgat gcaaactttt acgtgtgccc accccccacg   360
```

```
ggcgccacgg tggtgcagtt cgagcagccg cgccgctgcc cgacccggcc cgagggtcag      420
aactacacgg agggcatcgc ggtggtcttc aaggagaaca tcgccccgta caagttcaag      480
gccaccatgt actacaaaga cgtcaccgtt tcgcaggtgt ggttcggcca ccgctactcc      540
cagtttatgg ggatctttga ggaccgcgcc cccgtcccct cgaggaggt gatcgacaag       600 atcaacgcca agggggtctg tcggtccacg gccaagtacg tgcgcaacaa cctggagacc      660
accgcgtttc accgggacga ccacgagacc gacatggagc tgaaaccggc caacgccgcg      720
acccgcacga gccggggctg gcacaccacc gacctcaagt acaacccctc gcgggtggag      780
gcgttccacc ggtacgggac gacggtaaac tgcatcgtcg aggaggtgga cgcgcgctcg      840
gtgtacccgt acgacgagtt tgtgttggcg actggcgact ttgtgtacat gtccccgttt      900
tacggctacc gggaggggtc gcacaccgaa cacaccagct acgccgccga ccgcttcaag      960
caggtcgacg gcttctacgc gcgcgacctc accaccaagg cccgggccac ggcgccgacc     1020
acccggaacc tgctcacgac ccccaagttc accgtggcct gggactgggt gccaaagcgc     1080
ccgtcggtct gcaccatgac caagtggcag gaggtggacg agatgctgcg ctccgagtac     1140
ggcggctcct tccgattctc ttccgacgcc atatccacca ccttcaccac caacctgacc     1200
gagtacccgc tctcgcgcgt ggacctgggg gactgcatcg gcaaggacgc ccgcgacgcc     1260
atggaccgca tcttcgcccg caggtacaac gcgacgcaca tcaaggtggg ccagccgcag     1320
tactacctgg ccaatggggg ctttctgatc gcgtaccagc cccttctcag caacacgctc     1380
gcggagctgt acgtgcggga acacctccgc gagcagagcc gcaagccccc aaaccccacg     1440
cccccgccgc ccggggccag cgccaacgcg tccgtggagc gcatcaagac cacctcctcc     1500
atcgagttcg ccaggctgca gtttacgtac aaccacatac agcgccatgt caacgatatg     1560
ttgggccgcg ttgccatcgc gtggtgcgag ctgcagaatc acgagctgac cctgtggaac     1620
gaggcccgca agctgaaccc caacgccatc gcctcggcca ccgtgggccg gcgggtgagc     1680
gcgcggatgc tcgcgacgt gatggccgtc tccacgtgcg tgccggtcgc cgcggacaac     1740
gtgatcgtcc aaaactcgat gcgcatcagc tcgcggcccg gggcctgcta cagccgcccc     1800
ctggtcagct ttcggtacga agaccagggc ccgttggtcg aggggcagct gggggagaac     1860
aacgagctgc ggctgacgcg cgatgcgatc gagccgtgca ccgtgggaca ccggcgctac     1920
ttcaccttcg gtggggcta cgtgtacttc gaggagtacg cgtactccca ccagctgagc     1980
cgcgccgaca tcaccaccgt cagcaccttc atcgacctca acatcaccat gctggaggat     2040
cacgagtttg tccccctgga ggtgtacacc gccacgaga tcaaggacag cggcctgctg      2100
gactacacgg aggtccagcg ccgcaaccag ctgcacgacc tgcgcttcgc cgacatcgac     2160
acggtcatcc acgccgacgc caacgccgcc atgtttgcgg gcctgggcgc gttcttcgag     2220
gggatgggcg acctggggcg cgcggtcggc aaggtggtga tgggcatcgt gggcggcgtg     2280
gtatcggccg tgtcgggcgt gtcctccttc atgtccaacc cctttggggc gctgccgtg      2340 ggtctgttgg tcctggccgg cctggcggcg gccttcttcg cctttcgcta cgtcatgcgg     2400
ctgcagagca accccatgaa ggccctgtac ccgctaacca ccaaggagct caagaacccc     2460
accaacccgg acgcgtccgg ggagggcgag gagggcggcg actttgacga ggccaagcta     2520
gccgaggccc gggagatgat acggtacatg gccctggtgt ctgccatgga gcgcacggaa     2580
cacaaggcca agaagaaggg cacgagcgcg ctgctcagcg ccaaggtcac cgacatggtc     2640
atgcgcaagc gccgcaacac caactacacc caagttccca acaaagacgg tgacgccgac     2700
gaggacgacc tgtgat                                                      2716
```

<210> SEQ ID NO 4
<211> LENGTH: 2716
<212> TYPE: DNA
<213> ORGANISM: herpes simplex virus type 2

<400> SEQUENCE: 4

```
atgcgcgggg ggggcttgat ttgcgcgctg gtcgtggggg cgctggtggc cgcggtggcg      60
tcggcggccc cggcggcccc ggcggccccc cgcgcctcgg gcggcgtggc cgcgaccgtc     120
gcggcgaacg gggtcccgc ctcccggccg ccccccgtcc cgagcccgc gaccaccaag      180
gcccggaagc ggaaaaccaa aaagccgccc aagcggcccg aggcgacccc gcccccgac      240
gccaacgcga ccgtcgccgc cggccacgcc acgctgcgcg cgcacctgcg ggaaatcaag     300
gtcgagaacg ccgatgccca gttttacgtg tgcccgcccc cgacgggcgc cacggtggtg     360
cagtttgagc agccgcgccg ctgcccgacg cgcccggagg ggcagaacta cacggagggc     420
atcgcggtgg tcttcaagga gaacatcgcc ccgtacaaat tcaaggccac catgtactac     480
aaagacgtga ccgtgtcgca ggtgtggttc ggccaccgct actcccagtt tatggggata     540
ttcgaggacc gcgcccccgt tcccttcgag gaggtgatcg acaagattaa caccaagggg     600
gtctgccgct ccacggccaa gtacgtgcgg aacaacatgg agaccaccgc gtttcaccgg     660
gacgaccacg agaccgacat ggagctcaag ccggcgaagg tcgccacgcg cacgagccgg     720
gggtggcaca ccaccgacct caagtacaac ccctcgcggg tggaggcgtt ccatcggtac     780
ggcacgacgg tcaactgcat cgtcgaggag gtggacgcgc ggtcggtgta cccgtacgat     840
gagtttgtgc tggcgacggg cgactttgtg tacatgtccc cgttttacgg ctaccgggag     900
gggtcgcaca ccgagcacac cagctacgcc gccgaccgct tcaagcaggt cgacggcttc     960
tacgcgcgcg acctcaccac gaaggcccgg gccacgtcgc cgacgacccg caacttgctg    1020
acgacccca gtttaccgt ggcctgggac tgggtgccga agcgaccggc ggtctgcacc     1080
atgaccaagt ggcaggaggt ggacgagatg ctccgcgccg agtacggcgg ctccttccgc    1140
ttctcctccg acgccatctc gaccaccttc accaccaacc tgaccgagta ctcgctctcg    1200
cgcgtcgacc tgggcgactg catcggccgg gatgcccgcg aggccatcga ccgcatgttt    1260
gcgcgcaagt acaacgccac gcacatcaag gtgggccagc gcagtacta cctggccacg    1320
gggggcttcc tcatcgcgta ccagcccctc ctcagcaaca cgctcgccga gctgtacgtg    1380
cgggagtaca tgcgggagca ggaccgcaag ccccggaatg ccacgcccgc gccactgcgg    1440
gaggcgccca gcgccaacgc gtccgtggag cgcatcaaga ccacctcctc gatcgagttc    1500
gcccggctgc agtttacgta taccacata cagcgccacg tgaatgacat gctggggcgc    1560
atcgccgtcg cgtggtgcga gctgcagaac cacgagctga ctctctggaa cgaggcccgc    1620
aagctcaacc ccaacgccat cgcctccgcc accgtcggcc ggcgggtgag cgcgcgcatg    1680
ctcggagacg tcatggccgt ctccacgtgc gtgcccgtcg ccccggacaa cgtgatcgtg    1740
cagaactcga tgcgcgtcag ctcgcggccg gggacgtgct acagccgccc cctggtcagc    1800
tttcggtacg aagaccaggg cccgctgatc gaggggcagc tgggcgagaa caacgagctg    1860
cgcctcaccc gcgacgcgct cgagccgtgc accgtgggcc accggcgcta cttcatcttc    1920
ggcggggggct acgtgtactt cgaggagtac gcgtactctc accagctgag tcgcgccgac    1980
gtcaccaccg tcagcacctt catcgacctg aacatcacca tgctggagga ccacgagttt    2040
gtgccctgg aggtctacac gccgccacgag atcaaggaca cgcggcctgct ggactacacg    2100
gaggtccagc gccgcaacca gctgcacgac ctgcgctttg ccgacatcga cacggtcatc    2160
```

```
cgcgccgacg ccaacgccgc catgttcgcg gggctgtgcg cgttcttcga ggggatgggg      2220
gacttggggc gcgcggtcgg caaggtagtc atgggagtag tggggggcgt ggtgtcggcc      2280
gtctcgggcg tgtcctcctt tatgtccaac cccttcgggg cgcttgccgt ggggctgctg      2340
gtcctggccg gcctggtcgc ggccttcttc gccttccgct acgtcctgca actgcaacgc      2400
aatcccatga aggccctgta tccgctcacc accaaggaac tcaagacttc cgaccccggg      2460
ggcgtgggcg gggaggggga ggaaggcgcg gaggggggcg ggtttgacga ggccaagttg      2520
gccgaggccc gagaaatgat ccgatatatg gctttggtgt cggccatgga gcgcacggaa      2580
cacaaggcca gaaagaaggg cacgagcgcc ctgctcagct ccaaggtcac caacatggtt      2640
ctgcgcaagc gcaacaaagc caggtactct ccgctccaca acgaggacga ggccggagac      2700
gaagacgagc tctaag                                                     2716

<210> SEQ ID NO 5
<211> LENGTH: 18
<212> TYPE: DNA
<213> ORGANISM: herpes simplex virus

<400> SEQUENCE: 5
ttctgcagct cgcaccac                                                   18

<210> SEQ ID NO 6
<211> LENGTH: 19
<212> TYPE: DNA
<213> ORGANISM: herpes simplex virus

<400> SEQUENCE: 6
ggagcgcatc aagaccacc                                                  19

<210> SEQ ID NO 7
<211> LENGTH: 31
<212> TYPE: DNA
<213> ORGANISM: herpes simplex virus type 1

<400> SEQUENCE: 7
cgatggcaac gcggcccaac atatcgttga c                                    31

<210> SEQ ID NO 8
<211> LENGTH: 27
<212> TYPE: DNA
<213> ORGANISM: herpes simplex virus type 2

<400> SEQUENCE: 8
cgatgcgccc cagcatgtcg ttcacgt                                         27

<210> SEQ ID NO 9
<211> LENGTH: 27
<212> TYPE: DNA
<213> ORGANISM: herpes simplex virus type 2

<400> SEQUENCE: 9
cgatgcgccc cagcatgtca ttcacgt                                         27

<210> SEQ ID NO 10
<211> LENGTH: 20
<212> TYPE: DNA
<213> ORGANISM: herpes simplex virus

<400> SEQUENCE: 10
ctggtcagct ttcggtacga                                                 20
```

```
<210> SEQ ID NO 11
<211> LENGTH: 20
<212> TYPE: DNA
<213> ORGANISM: herpes simplex virus

<400> SEQUENCE: 11
caggtcgtgc agctggttgc                                          20

<210> SEQ ID NO 12
<211> LENGTH: 15
<212> TYPE: DNA
<213> ORGANISM: herpes simplex virus

<400> SEQUENCE: 12
ccttgatctc gtggc                                               15
```